US008247648B2

(12) United States Patent
Newman et al.

(10) Patent No.: US 8,247,648 B2
(45) Date of Patent: Aug. 21, 2012

(54) BIOLOGICAL CONTROL OF PATHOGENICITY IN MICROBES THAT USE ALPHA, BETA UNSATURATED FATTY ACID SIGNAL MOLECULES

(75) Inventors: Karyn L. Newman, Berkeley, CA (US); Steven E. Lindow, Walnut Creek, CA (US)

(73) Assignee: The Regents of the University of California, Oakland, CA (US)

(*) Notice: Subject to any disclaimer, the term of this patent is extended or adjusted under 35 U.S.C. 154(b) by 373 days.

(21) Appl. No.: 12/422,825

(22) Filed: Apr. 13, 2009

(65) Prior Publication Data
US 2009/0227028 A1 Sep. 10, 2009

Related U.S. Application Data

(62) Division of application No. 11/157,469, filed on Jun. 20, 2005, now abandoned.

(60) Provisional application No. 60/580,786, filed on Jun. 18, 2004.

(51) Int. Cl.
C12N 15/09 (2006.01)
C12N 15/82 (2006.01)
C12N 15/31 (2006.01)
A01H 5/00 (2006.01)

(52) U.S. Cl. ........ 800/279; 800/278; 800/288; 800/298; 800/320.2; 800/306; 800/317

(58) Field of Classification Search .................. None
See application file for complete search history.

(56) References Cited

U.S. PATENT DOCUMENTS

| 4,855,230 | A | 8/1989 | Lindow |
| 4,877,438 | A | 10/1989 | Lindow |
| 7,205,452 | B2 * | 4/2007 | Zhang et al. .................. 800/279 |
| 2002/0028228 | A1 | 3/2002 | Bergstrom et al. |

OTHER PUBLICATIONS

Chetterjee et al (2002). Molecular-Plant Microbe Interactions 15:463-71.*
Piette et al (1984) Proc. Natl. Acad. Sci. USA 81:4134-38.*
Kilstrup et al (1988). Eur. J. Biochem 176:421-29.*
Kwon et al (1994) . J. Bacteriol. 176:2432.*
Martinussen et al (1998) 4380-86.*
Slater, H., et al., "A two-component system involving an HD-GYP domain protein links cell-cell signaling to pathogenicity gene expression in *Xanthomonas campestris*", Molecular Microbiology 38:986-1003.
U.S. Office Action dated Nov. 2, 2007 issued in U.S. Appl. No. 11/157,469.
U.S. Office Action (Final) dated Nov. 2, 2007 issued in U.S. Appl. No. 11/157,469.
U.S. Notice of Panel Decision from Pre-Appeal Brief Review dated Feb. 26, 2009 issued in U.S. Appl. No. 11/157,469.

Barber, C. E. et al. A novel regulatory system required for pathogenicity of *Xanthomonas campestris* is mediated by a small diffusible signal molecule. Molecular Microbiology 24, 555-66 (1997).
Bextine, B. R., et al., "Delivery of a Genetically Marked *Alcaligenes* sp. to the Glassy-Winged Sharpshooter for Use in a Paratransgenic Control Strategy", Current Microbiology 48, 327-31 (2004).
Dong et al., Nature, 2001, vol. 41 1, p. 813-817.
Dow, et al., "*Xylella* genomics and bacterial pathogenicity to plants", Yeast 2000; 17:263-71.
Dow, J. M. et al., "Biofilm dispersal in *Xanthomonas campestris* is controlled by cell-cell signaling and is required for full virulence to plants," Proc Natl Acad Sci USA Sep. 16, 2003, vol. 100, No. 19, pp. 10995-1000.
Hill, et al., "Multiplication and movement of *Xylella fastidiosa* within grapevine and four other plants," Phytopathology 85, 1368-1372 (1995).
Huynh, et al., "Bacterial Blight of Soybean Regulation of a Pathogen Gene Determining Host Cultivar Specificity," Science 245, 1374-1376 (1989).
Larsen, R. A., et al., "Genetic analysis of pigment biosynthesis in *Xanthobacter autotrophicus* Py2 using a new, highly efficient transposon mutagenesis system that is functional in a wide variety of bacteria", Arch Microbiol 178, 193-201 (2002).
Newman and Lindow, Abstract for American Phytopathological Society Meeting (Submitted, May 2004), Jul. 31-Aug. 4, 2004.
Newman and Lindow, Management of Pierce's disease of grape by interfering with cell-cell communication in *Xylella fastidiosa*, Research Progress Report, Q4, 2004.
Newman and Lindow, Management of Pierce's disease of grape by interfering with cell-cell communication in *Xylella fastidiosa*, Research Progress Report, Q4, 2003.
Newman and Lindow, Management of Pierce's disease of grape by interfering with cell-cell communication in *Xylella fastidiosa*, Research Progress Report, Q4, 2002.
Newman and Lindow, The Role of Cell-Cell Signaling in Host Colonization by *Xylella fastidiosa*, Research Progress Report, Q4, 2001
Newman et al., "Induction of Hydroxycinnamoyl-Tyramine Conjugates in Pepper by *Xanthomonas campestris*, a Plant Defense Response Activated by hrp Gene-Dependent and hrp Gene-Independent Mechanisms," MPMI vol. 14, No. 6, 2001, pp. 785-792.
Newman, K. L., et al., "Cell-cell signaling controls *Xylella fastidiosa* interactions with both insects and plants", Proc. Natl. Acad. Sci. USA 101, 1737-1742 (2004).
Park et al., "AhlD, an N-acylhomoserine lactonase in *Arthrobacter* sp., and predicted homologues in other bacteria", Microbiology (2003), 149, 1541-1550.

(Continued)

Primary Examiner — Medina A Ibrahim
(74) Attorney, Agent, or Firm — Emily M. Haliday; Weaver Austin Villeneuve & Sampson LLP

(57) ABSTRACT

DSF-based microbial pathogens may be controlled by certain methods and compositions. A method of controlling diseases caused in a host organism by pathogenic microbial expression of α,β unsaturated fatty acid signal (DSF) molecules involves inoculating the host organism with a non-pathogenic microbe that disrupts α,β unsaturated fatty acid signal molecule-mediated cell-cell communication by the pathogenic microbe in the host organism. Microbes having protein expression that interferes with α,β unsaturated fatty acid signal molecule-mediated cell-cell communication by the pathogenic microbe in the host organism can be identified and isolated or engineered by transformation with DSF-interference (inhibition or activation) gene or genes. Genes conferring DSF-interference activity can also be expressed in organisms (e.g., plants) susceptible to diseases caused by microbes that use DSF, resulting in genetically resistant organisms.

23 Claims, 14 Drawing Sheets

OTHER PUBLICATIONS

Park, et al., "Efficient and genotype-independent *Agrobacterium*-mediated tomato transformation," *J Plant Physiol* 160, 1253-7 (2003).

Scarpari, et al., "Expression of putative pathogenicity-related genes in *Xylella fastidiosa* grown at low and high cell density conditions in vitro," *FEMS Microbiol Lett* 222, 83-92 (2003). .

Shapiro et al., Florida Entomologist, 1998, vol. 81, No. 2, p. 201-210.

Simpson, et al. "The genome sequence of the plant pathogen *Xylella fastidiosa*", Nature, vol. 406, Jul. 13, 2000, pp. 151-157.

Slater, H., et al., "A two-component system involving an HD-GYP domain protein links cell-cell signaling to pathogenicity gene expression in *Xanthomonas campestris*", Molecular Microbiology 38:986-1003, (2000).

Vojnov et al., "Expression of the *gum* Operon Directing Xanthan Biosynthesis in *Xanthomonas campestris* and Its Regulation in Planta," MPMI vol. 14, No. 6, 2001, pp. 768-774.

Wang, et al., "A bacterial cell-cell communication signal with cross-kingdom structural analogues", Molecular Microbiology, 2004, 51 (3), 903-912.

Whitehead et al., "Quorum-sensing in Gram-negative bacteria," *FEMS Microbiology Reviews* 25, 365-404 (2001).

Whitehead et al., "Silencing the majority—Transgenic plants expressing an enzyme that degrades microbial signaling molecules show promise in controlling damage caused by bacterial infections", Nature Publishing Group, Aug. 2001, vol. 19, pp. 735-736.

\* cited by examiner

- *rpfF* mutant cells may be unable to escape as efficiently as the wild type
- completely blocked vessels would increase in frequency
- symptom development, which is tightly correlated with frequency of blocked vessels, would increase

Average lesion length in mustard seedlings

FIG. 18

Average proportion of vines with disease

FIG. 19

BIOLOGICAL CONTROL OF PATHOGENICITY IN MICROBES THAT USE ALPHA, BETA UNSATURATED FATTY ACID SIGNAL MOLECULES

CROSS-REFERENCE TO RELATED APPLICATIONS

This application is a divisional of U.S. application Ser. No. 11/157,469, filed Jun. 20, 2005, which claims priority to U.S. Provisional Patent Application No. 60/580,786, filed Jun. 18, 2004, titled BIOLOGICAL CONTROL OF PATHOGENICITY IN MICROBES THAT USE ALPHA, BETA UNSATURATED FATTY ACID SIGNAL MOLECULES, each of which is incorporated herein by reference for all purposes.

BACKGROUND OF THE INVENTION

The present invention relates generally methods and compositions for control of microbial pathogens.

Species of *Xanthomonas* (*Xanthomonas* spp.) are responsible for major agricultural diseases. For example, members of the Brassicaceae, which includes broccoli, cabbage and other plants, are susceptible to black rot, which is caused by *Xanthomonas campestris* pathovar *campestris* (Xcc); members of the Solanaceae, which includes tomatoes and peppers, are susceptible to bacterial spot, which is caused by *X. campestris* pathovar *vesicatoria* (Xcv); and rice is subject to bacterial leaf blight, which is caused by *X. oryzae* pathovar *oryzae* (Xoo). Many other important commercial crops are susceptible to diseases caused by *Xanthomonas* spp., including wheat, soybean, walnut, mango, peach and many ornamental crops.

Xcc is also known to be closely related to another pathogenic bacterial species, *Xylella fastidiosa* (Xf), which causes citrus variegated chlorosis, almond leaf scorch and Pierce's disease of grape. Again, several other important commercial crops are susceptible to diseases caused by *Xylella* spp., including almonds, peaches, plums, alfalfa, citrus, oak, maple, coffee and oleander. Pierce's disease, as a particular example, is a chronic problem in the grape industry in California, greatly exacerbated due to the introduction of the glassy-winged sharpshooter, which is a very effective vector of the Xf pathogen. The management of this disease is particularly problematic since vector control has not proven effective, and the nature of the colonization of grapevines by the pathogen limit the utility of bactericides in killing the pathogen and make strategies of disease control based on other bacterial diseases ineffective.

Improved methods and compositions for control of *Xanthomonad*, *Xylella*, and related microbial pathogens are needed.

SUMMARY OF THE INVENTION

The present invention relates generally methods and compositions for control of microbial pathogens by disrupting their ability to communicate via a particular class of small molecules.

Species of *Xanthomonas* and *Xylella* communicate using a class of small molecules, $\alpha,\beta$ unsaturated fatty acid signal molecules, which are termed diffusible signal factors (DSF), as signals. The signals, which increase in concentration with population density, typically coordinate the expression of genes involved in exploitation of a host organism. The virulence of the microbial pathogens is greatly reduced when the ability to produce signaling compounds is disrupted by mutation. The disruption may be by way of inhibition of DSF by degradation or blocking with an analog, or, since over-expression of DSF has also been shown to reduce virulence, activation/over-expression of DSF (e.g., with DSF synthase).

The present invention provides methods and compositions for control of DSF-based microbial pathogens. The methods and compositions of the invention draw on the findings that blocking cell-cell signaling in DSF-based pathogenic organisms reduces virulence (in the case of the *Xanthomonads*, for example) or spread (in the case of *Xylella*, for example) of the pathogen. Methods and materials for identifying DSF-interfering strains of bacteria have been developed and control of Xcc and Xf by inoculation of plants with the DSF-interfering strains has been established. In addition, construction of DSF transgenes and heterologous expression of DSF has been demonstrated. The elucidation of the bacterial mechanisms of Xf pathogenicity and the establishment of an associated DSF-based cell-cell signaling requirement allows extension of the principles of control based on DSF-based signal blocking from *Xanthomonads* to *Xylella*, even though the mechanisms are different.

In one aspect, the invention relates to a method of controlling diseases caused in a host organism by pathogenic microbial expression of $\alpha,\beta$ unsaturated fatty acid signal molecules. The method involves inoculating the host organism with a non-pathogenic microbe that disrupts $\alpha,\beta$ unsaturated fatty acid signal molecule-mediated cell-cell communication by the pathogenic microbe in the host organism.

In another aspect, the invention relates to the identification and isolation or manufacture of microbes having protein expression (express one or more proteins) that interferes with $\alpha,\beta$ unsaturated fatty acid signal molecule-mediated cell-cell communication by the pathogenic microbe in the host organism. The invention provides for the identification and isolation of naturally occurring microbes that have been identified as having the required DSF-interference property. The invention also provides for the construction of transgenic microbial cells having the required DSF-interference property. In the latter case, robust species particularly well-suited for large scale implementation biological control (i.e., vigorous non-pathogenic colonists of the host plant (the plant being protected)) may be transformed with DSF-interference gene or genes (i.e., coding sequence(s)).

In a further aspect, the invention relates to a host organism having cells transformed to have protein expression (express one or more proteins) that interferes with $\alpha,\beta$ unsaturated fatty acid signal molecule-mediated cell-cell communication by a pathogenic microbe in the host organism. Thus, genes (coding sequences) conferring DSF-interference activity can be expressed in organisms (e.g., plants) susceptible to diseases caused by microbes that use DSF, resulting in genetically resistant organisms.

These and other features of the invention are further described and exemplified in the detailed description below.

BRIEF DESCRIPTION OF THE DRAWINGS

FIGS. 18 and 19 illustrate DSF degradation reduces pathogenicity of Xcc and virulence of Xf, respectively.

DETAILED DESCRIPTION OF SPECIFIC EMBODIMENTS

Figure 1:
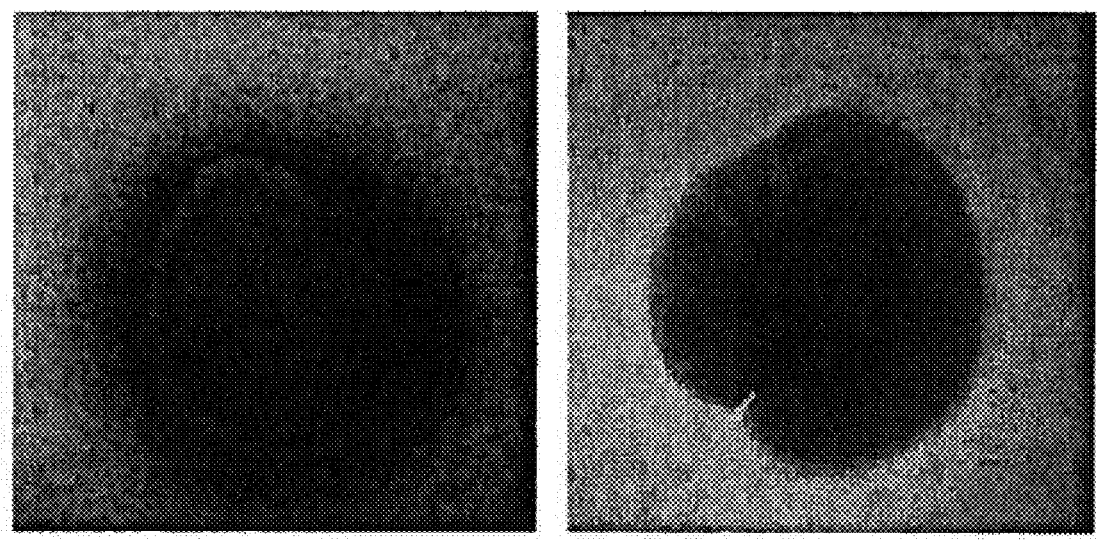
FIGS. 1, 2A and 2B illustrate the results of DSF biosensor assays in accordance with aspects of the present invention.

Reference will now be made in detail to specific embodiments of the invention. Aspects of the specific embodiments are illustrated in the accompanying drawings. While the invention will be described in conjunction with these specific embodiments, it will be understood that it is not intended to limit the invention to such specific embodiments. In the following description, numerous specific details are set forth in order to provide a thorough understanding of the present invention. The present invention may be practiced without some or all of these specific details. In other instances, well known process operations have not been described in detail in order not to unnecessarily obscure the present invention.

INTRODUCTION

In *Xanthomonas campestris* pathovar *campestris* (Xcc), the expression of pathogenicity genes is controlled by the Rpf system of cell-cell communication, enabling a population of cells to launch a pathogenic attack in a coordinated manner. Barber, C. E. et al. A novel regulatory system required for pathogenicity of *Xanthomonas campestris* is mediated by a small diffusible signal molecule. *Molecular Microbiology* 24, 555-66 (1997). A cluster of genes (called rpf for regulation of pathogenicity factors) of Xcc encode the components of a cell-cell communication system. The gene rpfF is involved in the production of a class of small molecules, α,β unsaturated fatty acid signal molecules, which are termed diffusible signal factors (DSF), as signals. DSF is released from cells and is required for production of an extracellular polysaccharide (EPS) and extracellular enzymes, which play a major role in pathogenicity, and therefore rpfF mutants are completely avirulent. As the population grows, the local concentration of DSF increases. Other Rpf proteins are thought to sense the increase in DSF concentration and transduce a signal, resulting in expression of pathogenicity factors involved in exploitation of a host organism. Whitehead Neil, A., Barnard Anne, M. L., Slater, H., Simpson Natalie, J. L. & Salmond George, P. C. Quorum-sensing in Gram-negative bacteria. *FEMS Microbiology Reviews* 25, 365-404 (2001). This coordinate expression of virulence traits in a cell-density dependent fashion, referred to as quorum sensing, presumably occurs because cells would not benefit from expression of virulence traits when in low numbers in a host. The expression of such traits by solitary cells would be futile and a deleterious waste of metabolic resources. Conversely, when part of a group, the protection afforded by expression of virulence traits would be mutually beneficial and hence cells express such traits only when in high numbers.

There is a very close phylogenetic relationship between plant pathogenic bacteria in the genus *Xanthomonas* and *Xylella fastidiosa* (Xf). Xf shares sequence similarity with Xcc; the Xf genome not only contains homologs of the rpf genes most essential for cell-cell signaling in Xcc, but also exhibits striking colinearity in the arrangement of these genes on the chromosome. Dow, J. M., and M. J. Daniels. 2000. *Xylella* genomics and bacterial pathogenicity to plants. Yeast 17:263-71; Simpson, A. J. G., F. C. Reinach, P. Arruda, et al. 2000. The genome sequence of the plant pathogen *Xylella fastidiosa*. Nature 406:151-157. The Xf genome lacks homologs of genes shown to be involved in production and perception of other known cell-cell signaling systems, such as the luxI/luxR genes and other genes shown to be involved in production and perception of AHLs. Crossman, L., Daniels, M. J. & Dow, M. in *Molecular Plant-Microbe Interactions* (Madison, Wis., 2001). Xf has also been shown to produce a diffusible signal that is recognized by Xcc. Scarpari, L. M., Lambais, M. R., Silva, D. S., Carraro, D. M. & Carrer, H. Expression of putative pathogenicity-related genes in *Xylella fastidiosa* grown at low and high cell density conditions in vitro. *FEMS Microbiol Lett* 222, 83-92 (2003).

It has now been established that the existence of a DSF-mediated cell-cell signaling system in Xf and the mechanism by which it operates. Unlike *Xanthomonads*, Xf requires insect vectors for spread from plant to plant. DSF signaling has been found to play a role in virulence and transmission of Xf. Xf rpfF mutants exhibit increased virulence to plants, however, they are unable to be spread from plant to plant by their insect vectors. Newman, K. L., Almeida, R. P. P., Purcell, A. H. & Lindow, S. E. Cell-cell signaling controls *Xylella fastidiosa* interactions with both insects and plants. *Proc. Natl. Acad. Sci. USA* 101, 1737-1742 (2004).

The present invention relates generally methods and compositions for control of microbial pathogens by disrupting DSF-mediated cell-cell communication. Disruption or interference of DSF-mediated cell-cell communication may be achieved by DSF inhibition or activation/over-expression. Inhibition may be achieved by the expression, e.g., by an isolated or engineered cell, of a protein that degrades DSF or expresses a non-functional DSF analog. Activation/over-expression may be achieved by providing additional DSF or DSF synthase, e.g., by isolated, mutated and/or engineered cells that over-expresses DSF.

The methods and compositions of the invention draw on the findings that blocking cell-cell signaling in DSF-based pathogenic organisms reduces virulence (in the case of the *Xanthomonads*, for example) or spread (in the case of *Xylella*, for example) of the pathogen. Methods and materials for identifying DSF-interfering strains of bacteria have been developed and control of Xcc and Xf by inoculation of plants with the DSF-interfering strains has been established. In addition, construction of DSF transgenes and heterologous expression of DSF has been demonstrated. The elucidation of the bacterial mechanisms of Xf pathogenicity and the establishment of an associated DSF-based cell-cell signaling requirement allows extension of the principles of control based on DSF-based signal blocking from *Xanthomonads* to *Xylella*, even though the mechanisms are different.

Disease Control Methods

In one aspect, the invention relates to a method of controlling diseases caused in a host organism by pathogenic microbial expression of α,β unsaturated fatty acid signal molecules. The method involves inoculating the host organism with a microbe that disrupts α,β unsaturated fatty acid signal molecule-mediated cell-cell communication by the pathogenic microbe in the host organism.

The method is particularly applicable in agricultural biological control applications where the host organism is a plant and the pathogenic microbe is bacterial. For example, members of the Brassicaceae, which includes broccoli, cabbage and other plants, are susceptible to black rot, which is caused by *Xanthomonas campestris* pathovar *campestris* (Xcc). Members of the Solanaceae, which includes tomatoes and peppers, are susceptible to bacterial spot, which is caused by *X. campestris* pathovar *vesicatoria* (Xcv). Rice is subject to bacterial leaf blight, which is caused by *X. oryzae* pathovar *oryzae* (Xoo). And *Xylella fastidiosa* (Xf) causes citrus variegated chlorosis, almond leaf scorch and Pierce's disease of grape.

Method of Identifying Interference Microbial Strains

Suitable bacterial strains for inoculation of host plants may be obtained from a variety of techniques. Naturally occurring microbial strains that have been identified as having the required DSF-interference property can be identified and isolated. For example, bacterial strains that can interfere with DSF signaling can be identified using a biosensor. Suitable biosensors include a bacterial strain that expresses its own DSF and emits a signal (e.g., fluoresces) unless DSF signaling is disrupted. Bacterial strains are applied to appropriate growth media with the biosensor and those strains possessing a DSF-inhibition property may be identified by weakening of the fluorescence signal. An example of this is illustrated with reference to FIG. 2B in Example 1, below.

DSF-activating strains can be identified by a second biosensor that cannot express DSF and can only emit a signal (e.g., fluoresce) if exogenous DSF is provided by the activating strain.

This second biosensor strain can also be used to verify that DSF-inhibiting strains can degrade DSF. Lack of fluorescent signal when DSF is added to a culture of the identified inhibition strain and subsequently tested with this biosensor confirms that the inhibitor cells were able to degrade the DSF that was added to the culture.

Such identified strains may then be isolated and cultured according to procedures well know to those of skill in the art for further use, for example in inoculation of plants for disease control.

Method of Constructing Interference Microbial Strains

Transgenic bacteria having the required DSF-interference property may also be constructed. Initially genes conferring DSF interference are isolated from wild bacterial strains. The genes may be isolated by a number of techniques, such as by transposon mutagenesis and screening for loss of DSF degradation ability followed by identification of the gene disrupted by the transposon. According to one example of this technique, a library of mutants can be obtained by diparental mating of each interference strain with *Eschericia coli* cells harboring pRL27, a suicide vector carrying a Tn5-derivative transposon. Larsen, R. A., Wilson, M. M., Guss, A. M. & Metcalf, W. W. Genetic analysis of pigment biosynthesis in *Xanthobacter autotrophicus* Py2 using a new, highly efficient transposon mutagenesis system that is functional in a wide variety of bacteria. *Arch Microbiol* 178, 193-201 (2002). Transposon insertion events confer kanamycin resistance to the host cell, allowing efficient selection of mutated cells. The resulting mutant collections can be screened for a loss of the ability to interfere with DSF signaling using a DSF biosensor-based screen, such as that described above. Once a DSF-interference mutant is identified, the gene disrupted by the Tn5-derivative transposon can be cloned and sequenced using the one-step cloning strategy described by Larsen et al. to identify the DSF-interference gene.

Alternatively, genes conferring DSF interference can be isolated from wild bacterial strains by construction and screening of cosmid libraries. According to this technique, for each strain, a cosmid library can be constructed in a plasmid (e.g., pLAFR3) (Huynh, T. V., Dahlbeck, D. & Staskawicz, B. J. Bacterial Blight of Soybean Regulation of a Pathogen Gene Determining Host Cultivar Specificity. Science 245, 1374-1376 (1989)) and screened for the ability to degrade DSF when introduced into *E. coli*, or if necessary *Xanthomonas campestris* pathovar campestris (Xcc), using the DSF biosensor-based screen, described above. Once a particular cosmid carrying the DSF-degrader gene is identified, the cosmid can be subjected to standard subcloning and insertional mutagenesis to narrow down which gene on the cosmid confers DSF-degradation activity. The identity of the gene can be revealed by sequencing of subcloned fragments.

Microbial Expression of DSF Interference (Activation or Inhibition)

The genes so isolated can then be used to transform suitable bacterial cells, which can then be used to inoculate the host plants. In one embodiment, in order to more effectively deliver DSF interference to the site of infection by the pathogen and facilitate large-scale application of biological control, bacteria that are vigorous non-pathogenic colonists of the plant being protected can be engineered to express DSF-degradation (inhibition) and DSF-synthesis (activation/over-expression) genes. Protection to plants threatened by *Xylella fastidiosa* (Xf), such as grapevines, may be best be provided by an endophytic bacterium (a bacterium that lives inside the plant body), such as *Alcaligenes xylosoxidans denitrificans* (Axd). Protection to plants threatened by *Xanthomonas* spp., such as tomato and broccoli, may be best protected by a vigorous epiphytic bacterium (a bacterium that lives on the surface of leaves), such as *Pseudomonas fluorescence* A506 (PfA506).

For DSF synthesis (activation/over-expression), the rpfF gene from Xf or Xcc can be placed under the control of the kanamycin resistance gene promoter from Tn903 or another suitable promoter and introduced into the Axd and PfA506 genomes. A protocol employing a transposon-containing plasmid, pSP14, to deliver genes directly into the chromosome of Axd and PfA506 may be used. Bextine, B. R., Lauzon, C. R., Potter, S. E., Lampe, D. & Miller, T. E. Delivery of a genetically marked *Alcaligenes* sp. to the glassy-winged sharpshooter for use in a paratransgenic control strategy. *Current Microbiology* 48, 327-31 (2004). For DSF inhibition, DSF-inhibition genes under the control of a constitutive promoter, such as the Kan promoter from Tn903, can be transferred into Axd and PfA506 by the same strategy.

Isolated, mutated and/or engineered DSF-interference microbial strains may be modified in accordance with conventional techniques to introduce novel genetic capabilities. These techniques, for the most part, involve transformation or conjugation. Various genetic capabilities which can provide advantages for the DSF-interference strains include imparting antibiotic resistance, bacteriocin production, host range, growth characteristics, e.g. colicin production, nitrogen fixation, or the like. By providing for a marker which allows for selection of transformants or conjugants, the desired organisms may then be selected. Markers include antibiotic resistance, colicin resistance, heavy metal resistance, providing prototrophy to auxotrophs, or the like.

Application of Microbes Expressing DSF Interference

Depending upon the nature of the plant, the part of the plant to which the DSF-interference strain is applied, as well as other factors, a variety of methods and compositions may be employed for application of the organism to the plant. In addition, it may be desirable to use mixtures of organisms, i.e., two or more DSF-interference strains, rather than a single organism.

*Xanthomonas* spp. are epiphytic, lending themselves to control by agents, for example, epiphytic cells with DSF-interference capability, applied to the surface of the plant. Transformed epiphytic bacterial cells, such as *Pseudomonas fluorescence* A506 (PfA506), carrying genes conferring DSF-interference capability, as described above, can be effectively introduced to plant hosts by topical application of a suitable formulation to the plants.

The number of cells per unit formulation will depend on whether the formulation is a dry or wet formulation. For wet formulation, e.g. foliar sprays, suspensions, aerosols, mist, etc., the number of cells per ml will generally be from about $10^5$ to $10^{10}$ cells per ml. Generally, it is desired to have about $10^4$ to $10^{10}$ cells/g fr. wt. of leaves during application. For dry formulations, the number of cells will generally range from about $10^4$ to $10^9$ cells/g of formulated product. The cells in the formulation should provide a sufficient number of cells to allow the cells to become established on the host plant with microorganisms present in the native environment taking into consideration the mortality rate, higher with spray formulations, which are encountered with the means of administration. The number of cells should be sufficient to colonize within about one week or less for sprays.

In aqueous formulations various additives may be included in minor amounts such as surfactants, e.g. nonionic, dyes, nutrients, buffers, penetrating agents for introducing the cells into the leaf, biological or chemical pesticides e.g. herbicides, insecticides, etc. In dry formulations various additives include inert powders, bacterial stabilizing agents, salts, anti-caking agents, nutrients, buffers, film forming materials, biological or chemical pesticides e.g. herbicides, insecticides, etc. The various additives will range in concentration from about $1 \times 10^{-4}$ to 1 weight percent.

One technique is to apply the DSF-interfering cells to the seed (seed inoculum) or seed piece of a plant. The bacteria may be formulated as a dry powder formulation in accordance with conventional techniques. Of particular interest is a powder formulation containing the cells, which is derived from combining about one part by volume of a cell containing gum suspension, with 4 volumes of an inert powdered carrier, e.g., talc. The gum suspension is prepared by combining about 1 vol. of a dense suspension of cells (about $10^9$-$10^{11}$ cells/ml) with about 10 vols. of a dilute magnesium salt solution, which mixture is then combined with 10 vols of a thick aqueous suspension of a natural gum. The gum will be about 90-99% by weight of the mixture and employed initially as a 10-30 weight percent suspension. The mixture is allowed to dry and ground to a fine powdered consistency. The seeds or seed pieces in a slightly moistened state are contacted with the powder. Upon planting, it is found that the bacteria colonize the emerging stem and leaves as they emerge from the soil.

The powder formulation may also be applied as a dust application. Conveniently, the bacteria are applied to the foliage at a rate of from about $10^7$ to $10^8$ bacteria per gram fr. wt. of leaves being inoculated. The use of the dust powder inoculation is particularly applicable during hot weather, on bright sunny days, when applied prior to mid to late afternoon and at low relative humidities.

Another way for establishing the DSF-interfering bacteria is by foliar spray. The bacteria need only be employed as an aqueous suspension, in substantial absence of other additives, e.g., nutrients and surfactants. The application rate will generally be approximately $10^6$ to $10^8$ cell/ml of vegetative cells in an aqueous suspension to provide about $10^4$ to cells/g. fr. wt. of leaves.

Since Xf is an endophytic bacterium, it is most effectively controlled by application of a control agent to the target plant host by a technique that delivers the control agent inside the plant body. Transformed endophytic bacterial cells, such as *Alcaligenes xylosoxidans denitrificans* (Axd), carrying genes conferring DSF-interference capability, as described above, can be introduced into grapevines by standard needle inoculation as described in Hill, B. L. & Purcell, A. H. Multiplication and movement of *Xylella fastidiosa* within grapevine and four other plants. *Phytopathology* 85, 1368-1372 (1995). While needle inoculation of individual plants may seem impractical in large scale agricultural application, the intensive nature of grape production lends itself to use of this technique, since individual plants are handled many times by workers during the course of the growing and harvesting seasons.

It has also been found that it is possible to establish large populations of bacteria within grape leaves, stems and petioles by simple topical applications of bacterial suspensions to plants in solutions of organosilicone surfactants having very low surface tensions. Non-endophytic bacterial species were also established in high numbers inside grape leaves and petioles following spray application to plants with a high concentration (e.g., about 0.2 to 1.0% V/V, for example about 0.5% to 1.0% of a silicon-based surfactant with a low surface tension (e.g., less than 25 dynes/cm), such as the product Break-Thru®, available from Goldschmidt Chemical Corporation.

Expression of DSF in Planta

In a further aspect, the invention relates to a host organism having cells transformed to have protein expression (express one or more proteins) that interferes with α,β unsaturated fatty acid signal molecule-mediated cell-cell communication by a pathogenic microbe in the host organism. Thus, genes conferring DSF-interference activity (activation/over-expression or inhibition) can be expressed in organisms (e.g., plants) susceptible to diseases caused by microbes that use DSF, resulting in genetically resistant organisms.

In one embodiment, the rpfF gene from Xf or Xcc (Genbank Accession Nos. NC_004556 (locus tag PD0407, gi:28056394) and Y09701, respectively) or other DSF-producing microbes can be placed under the control of the constitutive cauliflower mosaic virus 35S promoter or a ubiquitin promoter or other suitable promoter from the plant in a cassette on a binary vector capable of replication in both *E. coli* and *Agrobacterium tumefasciens*, pCAMBIA 2200 (The Centre for Application of Molecular Biology to International Agriculture (CAMBIA), GPO Box 3200, Canberra ACT 2601 Australia) and introduced into plant genomes using *A. tumefasciens*-mediated plant transformation by standard protocols, such as are described in Park, S. H., Morris, J. L., Park, J. E., Hirschi, K. D. & Smith, R. H. Efficient and genotype-independent *Agrobacterium*-mediated tomato transformation. *J Plant Physiol* 160, 1253-7 (2003).

Genbank Accession Nos. NC_004556 (locus tag PD0407, gi:28056394) (SEQ ID NO:1) and Y09701 (SEQ ID NO:2):

```
Xf rpfF:
translation = "MSAVHPIPHPICESSIRIIEETHRNVYWIYMHAHL

ARTTGAAYFSLKLIDDIMNYQSVLRQRLKEQTVQLPFVVLASDSNVFNLG

GDLQLFCDLIRRKEREALLDYACRCVRGAYAFHAGLNANVHSIALLQGNA

LGGGFEAALCCHTIVAEEGVMMGFPEVLFDLFPGMGAYSFMRQRISPKLA

ERLILEGNLYSSEELLAIGLIDKVVPRGKGIEAVEQIIRDSKRRQYTWAA

MQEVKKIAHEVSLEEMIRITELWVDSALKLSNKSLRTMERLIRAQQTHKN

TALKN"

Xcc rpfF:
translation = "MSAVQPFIRTNIGSTLRIIEEPQRDVYWIHMHADL

AINPGRACFSTRLVDDITGYQTNLGQRLNTAGVLAPHVVLASDSDVFNLG

GDLALFCQLIREGDRARLLDYAQRCVRGVHAFHVGLGARAHSIALVQGNA

LGGGFEAALSCHTIIAEEGVMMGLPEVLFDLFPGMGAYSFMCQRISAHLA

QKIMLEGNLYSAEQLLGMGLVDRVVPRGQGVAAVEQVIRESKRTPHAWAA

MQQVREMTTAVPLEEMMRITEIWVDTAMQLGEKSLRTMDRLVRAQSRRSG

LDAG"
```

DSF-inhibition genes under the control of the constitutive plant promoter may be transferred by the same strategy as outlined above.

EXPERIMENTAL

The invention having been generally described, may be better understood by reference to the following examples, which are provided for purposes of illustration and are not to be considered limiting of the invention.

Example 1

Identification and Effectiveness of DSF Interference Stains

A DSF signal sensing strain, or "DSF biosensor," carrying a green fluorescent protein (gfp) gene under the control of a promoter that is up-regulated in response to the DSF signal was engineered, as described in Newman, et al. *Proc. Natl. Acad. Sci. USA* 101, 1737-1742 (2004). A group of bacterial strains, "inhibitor strains," that can interfere with DSF signaling was identified using this biosensor. Results are shown in FIG. 1. The figure shows colonies of bacterial strains with (left panel) or without (right panel) DSF inhibition activity. Colonies are surrounded by a lawn of the DSF biosensor strain that expresses its own DSF and fluoresces green unless DSF signaling is disrupted. The dark halo around the colony in the left panel demonstrates inhibition of DSF signaling.

Figure 2A:
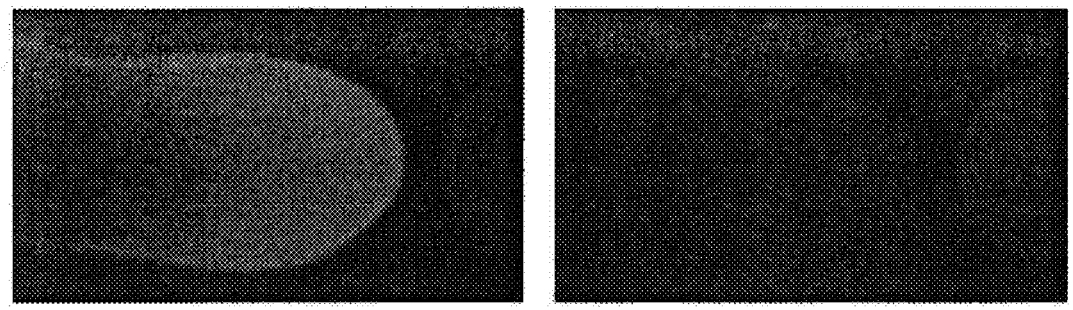

As illustrated in FIG. 2A, some of these strains interfere in signaling by degrading DSF. The figure illustrates degradation of DSF by an inhibitor strain. DSF was added to a liquid culture of the inhibitor strain (right panel) or to cell-free spent media from the same strain (left panel) and incubated overnight. The DSF remaining in the media after this treatment was extracted and plated to the right of a DSF biosensor that cannot express DSF, which can only fluoresce green if exogenous DSF is provided. The lack of fluorescence by the reporter in the right panel confirms that the inhibitor cells were able to degrade the DSF that was added to the culture.

Figure 2B:
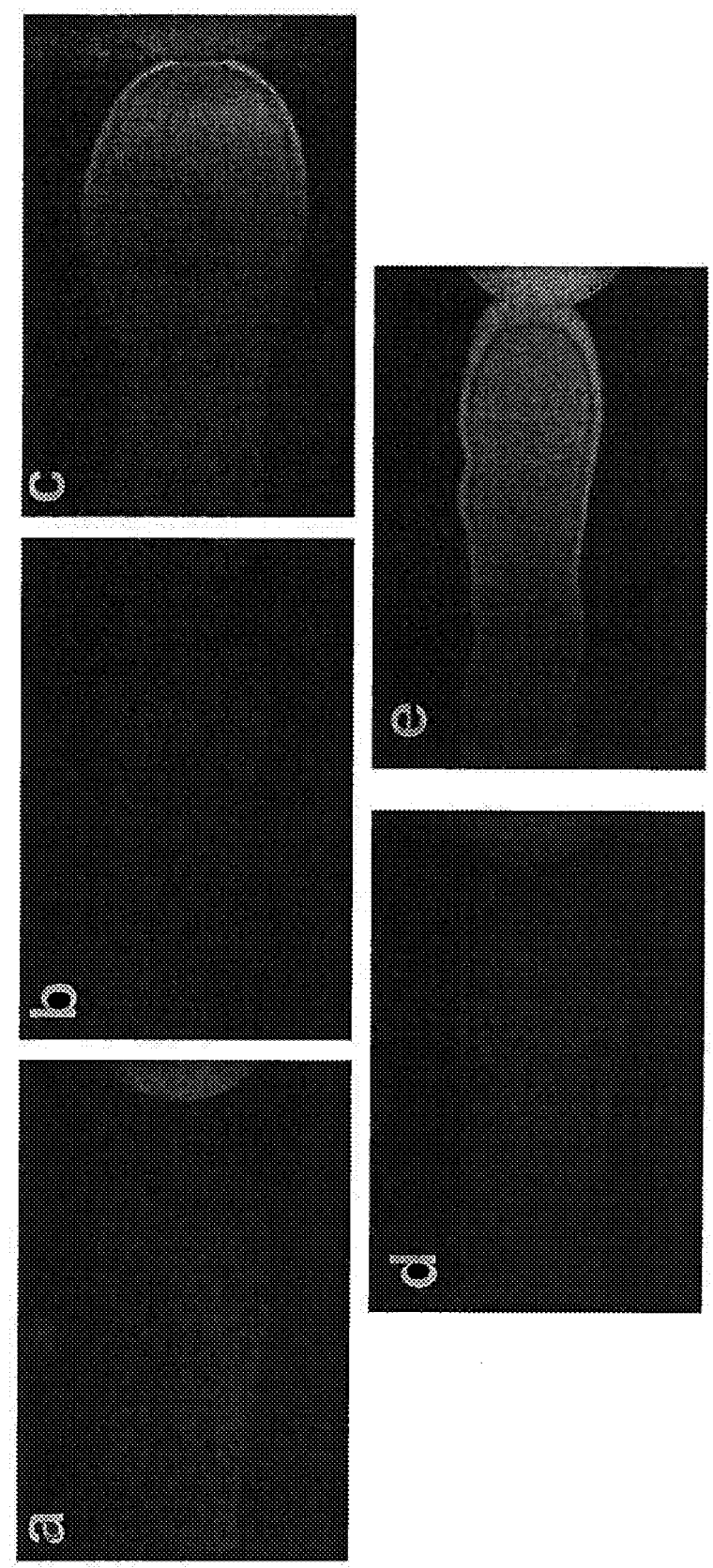

FIG. 2B provides additional evidence indicating that DSF is enzymatically degraded by some DSF-inhibiting strains. Crude protein extracts of several DSF-inhibiting strains were able to degrade DSF, while no degradation of DSF occurred when extracts were boiled prior to incubation with DSF, indicating that, in these strains, DSF-inhibition is likely due to enzymatic degradation of the signal. Other strains were unable to degrade DSF when it was added to growing cultures or crude protein extracts, indicating the existence of an alternate mechanism of DSF inhibition, such as synthesis of a DSF analog. FIG. 2B shows the results obtained with Strain G. Green fluorescence indicates DSF remaining after incubation with a culture (a), a crude protein extract (b), or a crude protein extract that was boiled (c). In panel d, no DSF was added to the culture and in panel e, no bacteria was inoculated into the culture.

Other inhibitor strains interfere via alternate mechanisms, which may include synthesis of a DSF analog. In addition, DSF interference may be achieved by synthesis of surplus DSF (over-expression).

Figure 3:
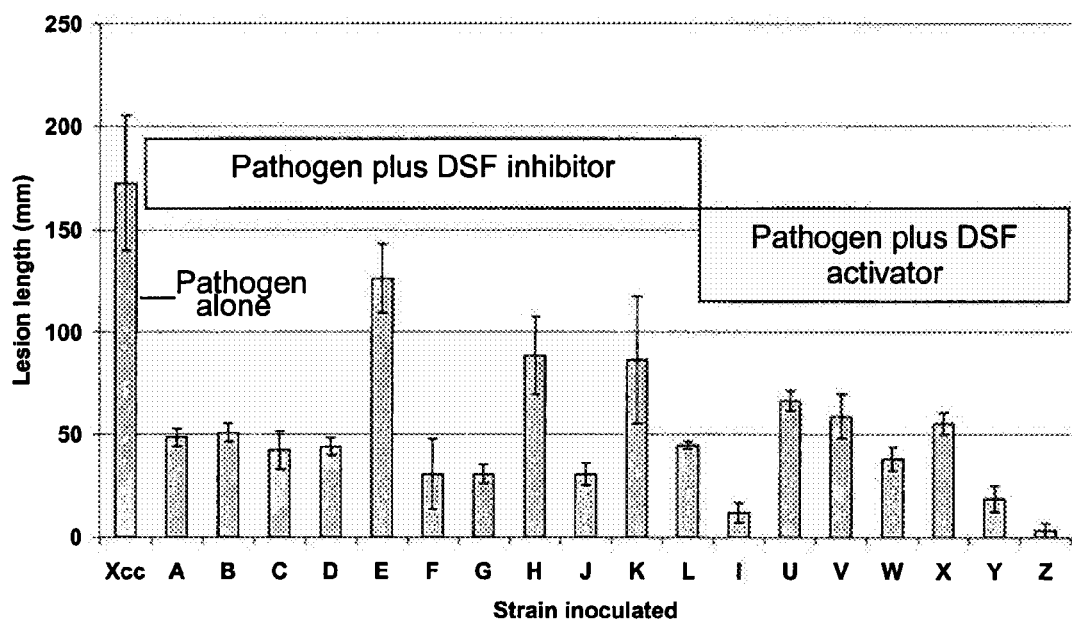
FIG. 3 illustrates control of black rot in cabbage by DSF-interfering bacteria in accordance with one aspect of the present invention.

The effectiveness of these strains in preventing disease in plants infected with DSF-producing pathogens was preliminarily tested for both *Xanthomonas* and *Xylella*. For *Xanthomonas*, control of black rot in cabbage by DSF-interfering bacteria was tested by inoculating cabbage seedlings with Xcc alone or co-inoculating with Xcc and the interfering strains. Results are shown in FIG. 3. The figure illustrates control of black rot in cabbage by DSF-interfering bacteria. Xcc strain 8004 was inoculated onto leaves of cabbage seedlings by the method of clipping leaves with scissors dipped in a solution of the pathogen (Dow, J. M. et al. Biofilm dispersal in *Xanthomonas campestris* is controlled by cell-cell signaling and is required for full virulence to plants. *Proc Natl Acad Sci USA* 100, 10995-1000 (2003)) and lesion length in these leaves was measured after 13 days (Xcc). Xcc was mixed with DSF-inhibiting (A-H, K, L) or DSF-activating (I, U-Z) strains prior to inoculation. Plants co-infected with the pathogen plus a DSF-interfering strain showed significantly reduced disease symptoms. Plants infected only with the DSF-producing strain showed no symptoms. Similar results were obtained with broccoli and turnip seedlings.

Figure 4:
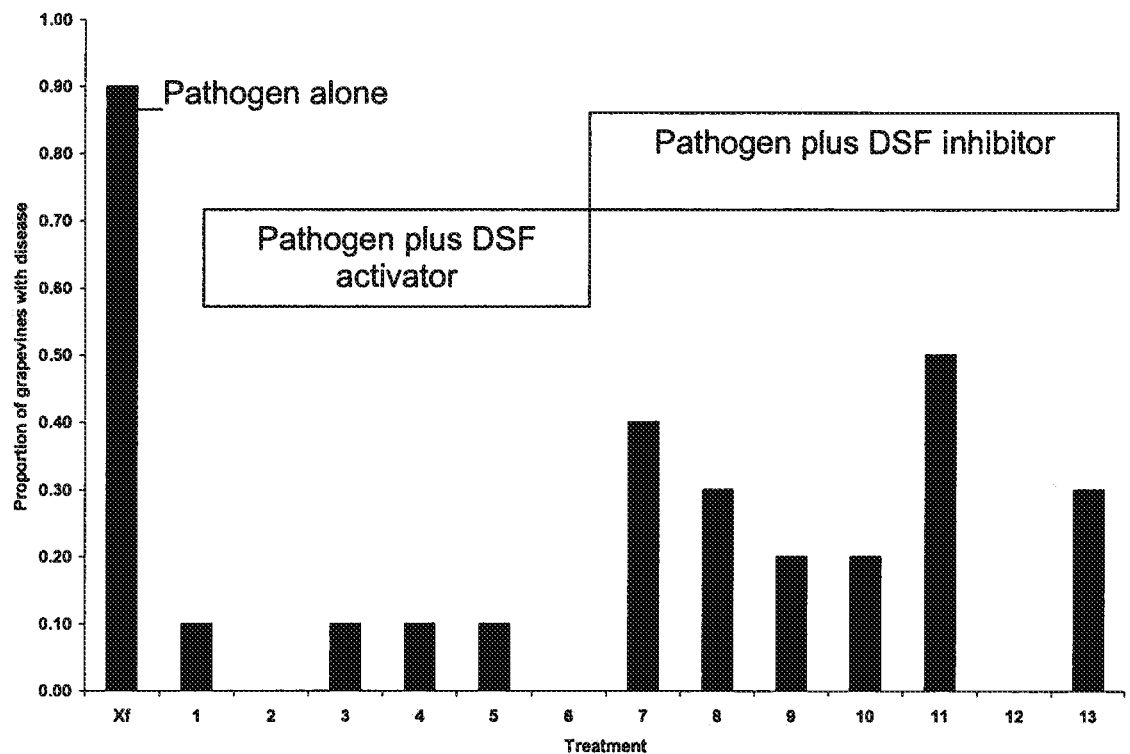
FIG. 4 illustrates the effects of treatments of Pierce's disease in plants inoculated with *Xylella fastidiosa* or Xf plus a signal interference strain in accordance with one aspect of the present invention.

FIG. 4 illustrates the effects of treatments of Pierce's disease in plants inoculated with *Xylella fastidiosa* (treatment Xf) or Xf plus a signal interference strain (treatments 1-13). Ten plants were inoculated with each treatment. While 90% of plants infected with the pathogen alone became diseased, significantly fewer plants were diseased when the pathogen was co-inoculated with a signal-interfering strain. Six of these strains are DSF activators (1-6), 6 are DSF inhibitors that degrade DSF (7-12), and 1 is a DSF inhibitor that does not degrade DSF (13). Similar results were seen in other repeat studies (see e.g., FIG. 12 in Example 3, below).

Both activator strains and inhibitor strains appeared effective in black rot and Pierce's disease control. These results provide a logical and practical basis for the expectation that these strains and their DSF-related activities will provide control of pathogenicity in DSF-producing disease organisms.

Example 2

Expression of DSF in Planta

DSF expression transgenes were constructed as follows. A 769 bp Hind III-Bgl II fragment containing the cauliflower mosaic virus 35S promoter was excised from pCAMBIA1201 and ligated into pCAMBIA1390 cut with Hind III and Bam HI to make pKLN1. The *Xylella fastidiosa* rpfF coding sequence was amplified directly from the *X. fastidiosa* genome using Pfu polymerase (Strategene) using primers "Xf rpfF F Nco I" (TACCATGGCCGCTGTACATCCCATTCCTCACCCCATAT) (SEQ ID NO:3) and "Xf rpfF R Bam HI" (CGGGATCCTCAGTTTTTTAGTGCTGTGTTTTTGTGAGTCT) (SEQ ID NO:4), cut with Nco I and Bam HI and ligated into pKLN1 cut with Nco I and Bgl II to make pKLN119. This plasmid carries a T-DNA that includes both hygromycin resistance and the *X. fastidiosa* rpfF gene driven by the CMV 35S promoter and followed by the NOS poly-A signal sequence.

pKLN119 and the empty vector pCAMBIA1390 were electroporated into *Agrobacterium* strain GV3101. *Nicotiana benthamiana* plants were transiently transformed by infiltration with suspensions of *Agrobacterium* harboring T-DNA construct pKLN119 or pCAMBIA1390.

Figure 5:
FIG. 5 illustrates the result of DSF biosensor assay in accordance with one aspect of the present invention.

Disks of infiltrated leaves were removed after two days, placed on KB agar plates and oversprayed with the DSF bioreporter strain 8525 (pKLN55). Green fluorescence indicates detection of DSF from the leaf disk. Results are shown in FIG. 5. The figure illustrates expression of DSF in *Nicotiana benthamiana*. In the left panel, the leaf disk infiltrated with pKLN119 is producing DSF, as shown by green fluorescence of the DSF bioreporter. In the right panel, the leaf disk infiltrated with pCAMBIA1390, the empty vector, does not cause gfp expression in the bioreporter, demonstrating that fluorescence is specific to expression of DSF.

These results demonstrate the principle that the DSF molecule can be synthesized by plant cells expressing the bacterial rpfF gene. Because expression by the plant was very robust, it is expected that expression can be achieved with ease in a variety of plant species.

Example 3

Studies of DSF Interference, and Inoculation and Transformation of Plants for Disease Control In this example, data is provided on the virulence of the wild-type *Xylella fastidiosa* strain and on a strain in which the rpfF gene encoding synthesis of DSF is being over-expressed with a kanamycin resistance gene promoter. The disease is much less in the plant in which Xf is over-expressing DSF (FIGS. 7 and 8), which correlates well with other information such as that blockage of DSF production increased virulence.

Figure 14:
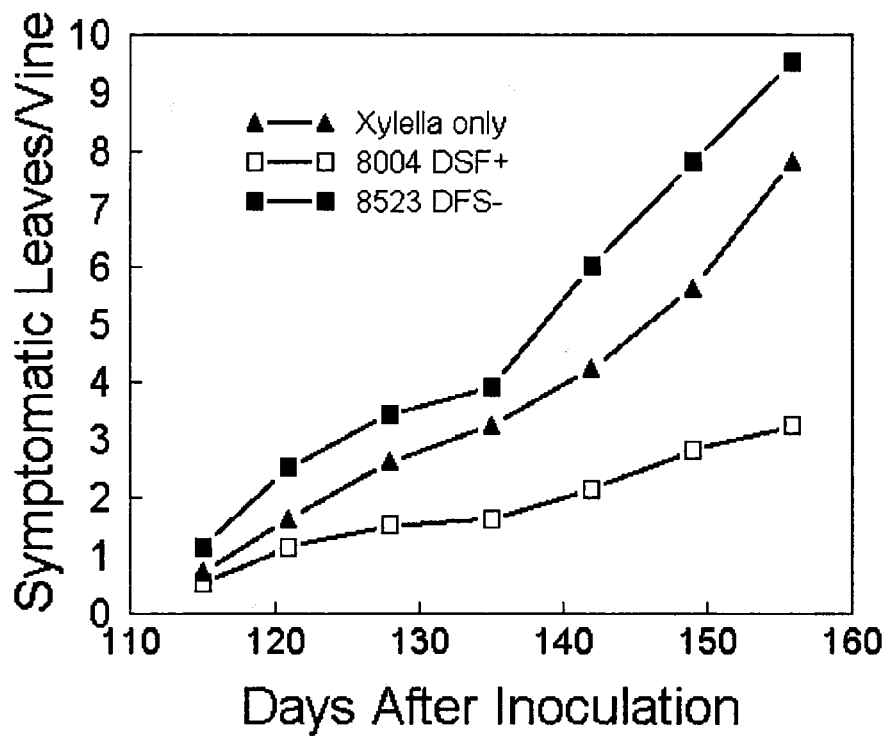
FIGS. 14-16 illustrate control of Pierce's disease of grape with bacterial strains that produce DSF in accordance with one aspect of the present invention compared with the control seen with mutants of these strains that can no longer produce DSF.
Figure 15:
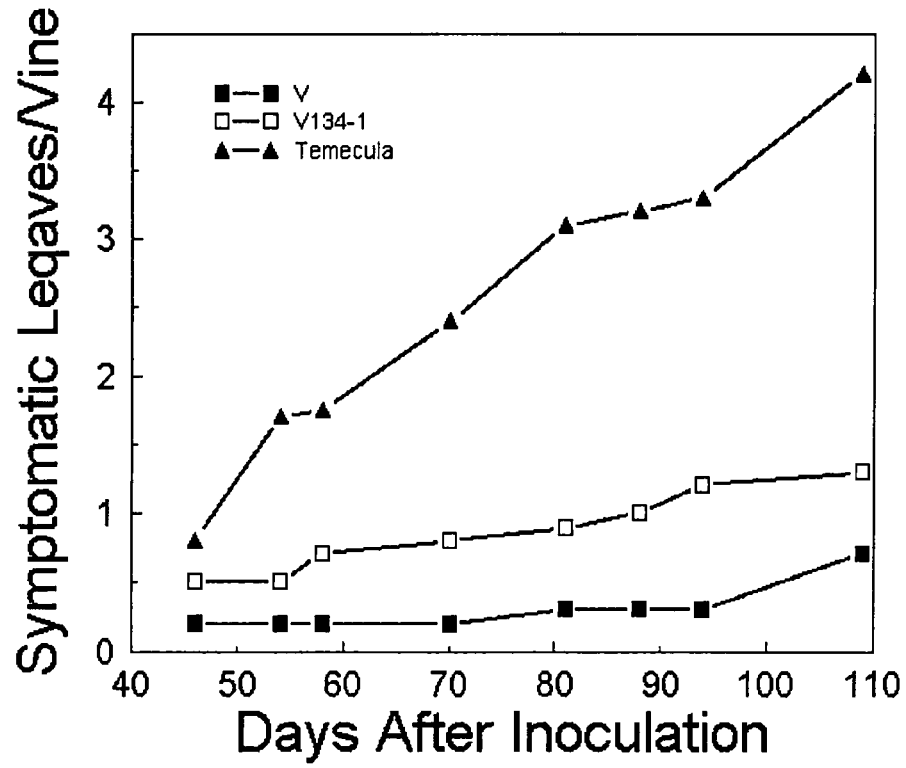
Figure 16:
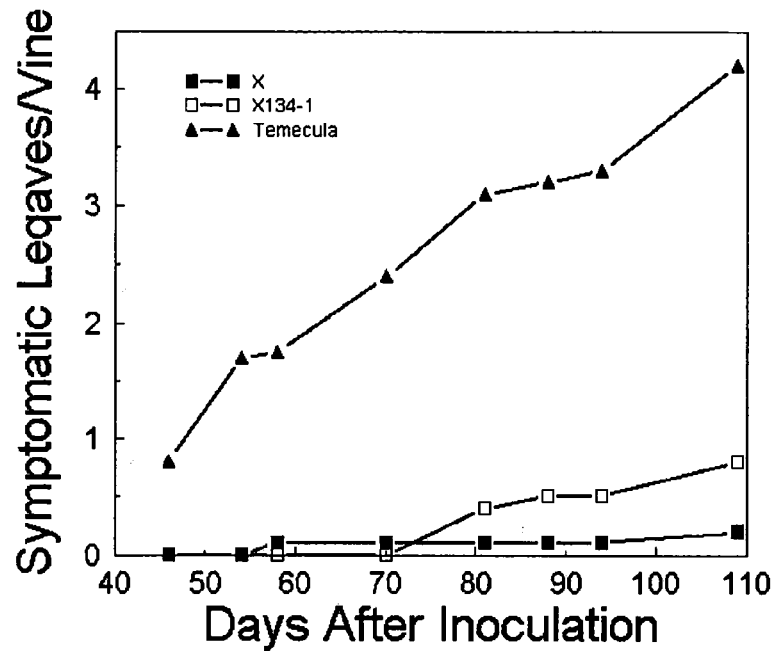
Figure 17:
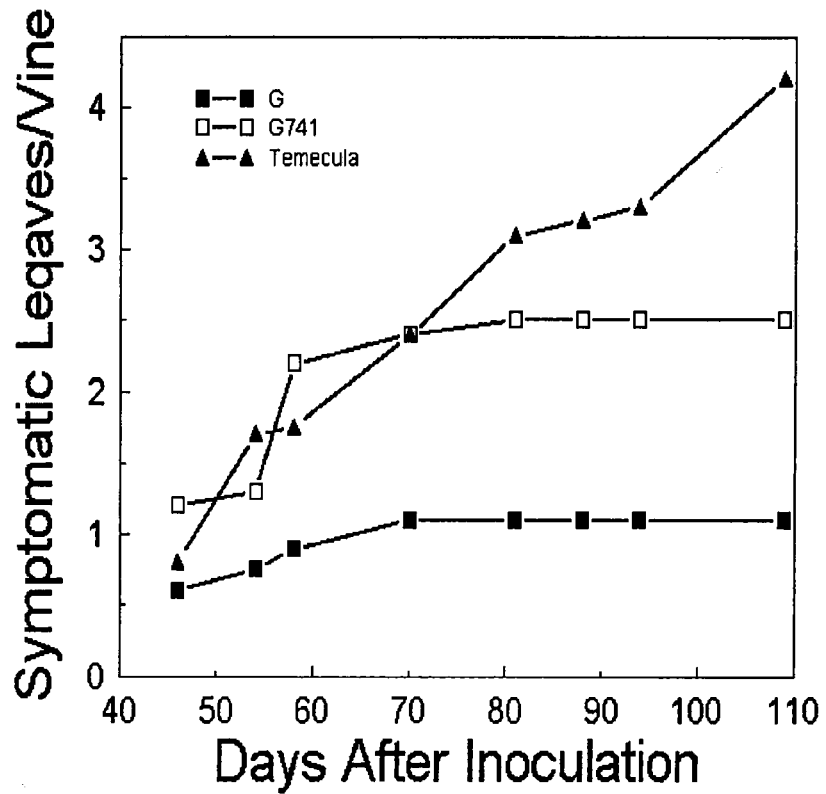
FIG. 17 illustrates that a mutant strain that no longer can degrade DSF is not as effective as its parental strain in controlling Pierce's disease of grape.

Control of Pierce's disease of grape with bacterial strains that produce DSF was also shown and compared with the control seen with mutants of these strains that can no longer produce DSF (FIGS. 14-16). The data showed that the mutants that no longer can produce DSF are not as effective in control of disease. Likewise, mutants of strain "G," a strain that no longer can degrade DSF, are not as effective as strain G in controlling Pierce's disease of grape (FIG. 17). Both of these sets of data suggest that altering levels of DSF in plants per se is what responsible for disease control.

Transgenic tomato and grape plants into which the rpfF genes of *Xylella fastidiosa* and *Xanthomonas campestris* have been introduced have also been generated.

Also, the use of an organosilicone surfactant with very low surface tension with bacterial suspensions to introduce bacteria that make or degrade DSF into plants was explored.

INTRODUCTION

DSF-mediated cell-cell signaling in Xf was investigated with the aim of developing cell-cell signaling disruption as a means of controlling Pierce's disease. It has been determined that the rpfF gene is necessary and sufficient for DSF signal synthesis and that rpfF mutants of Xf are hypervirulent and non-transmissible. Lack of transmissibility was linked to an inability of the rpfF mutant to form a biofilm in the insect foregut; while taken up by insects, the mutant strain is not retained. Xf strains that overproduce DSF produce disease symptoms in grape, but only at the site of inoculation and the cells do not move within the plant as do wild-type strains. Thus, it was hypothesized that elevating DSF levels in plants should reduce movement of Xf in the plant and also reduce the likelihood of transmission by sharpshooters. Several collections of bacterial strains isolated from plants were screened and identified bacterial strains that can interfere with Xf signaling both by producing large amounts of DSF, by degrading DSF, or by in some way interfering with recognition of DSF. When co-inoculated into grape with Xf, both DSF-producing strains and DFS degrading strains greatly reduced the incidence of disease in grape; DSF-producing strains consistently were the most effective in reducing disease.

Given that DSF appears to mediate an attenuation of virulence in Xf, it is hypothesized that it may be possible to transform grape with the rpfF gene to enable DSF production in planta in order to protect grape plants from Pierce's disease. Preliminary results indicate that transient expression of rpfF in *Nicotiana benthamiana* following infiltration with appropriate *Agrobacterium tumefaciens* strains resulted in high levels of DSF production, suggesting that it is likely that grape cells will produce DSF when transformed with the bacterial rpfF gene. Non-endophytic bacterial species were also established in high numbers inside grape leaves and petioles following spray application to plants with a high concentration of a silicon-based surfactant with a low surface tension suggesting that it may be possible to produce protective compounds such as DSF in plants by a variety of bacteria.

Figure 6:
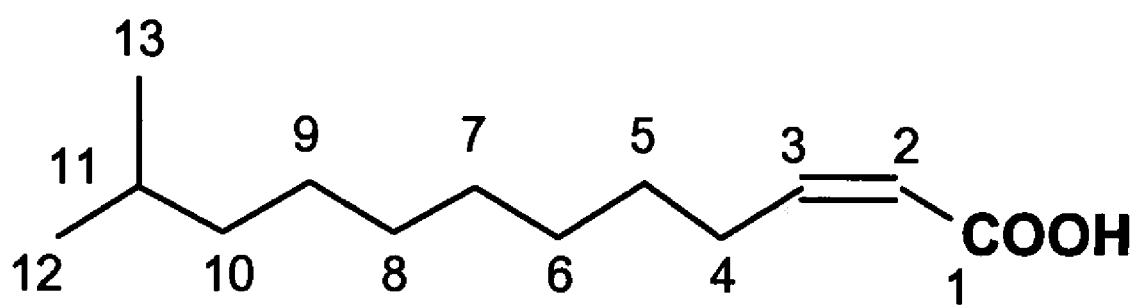
FIG. 6 illustrates the structure of a diffusible signal factor (DSF) (alpha,beta unsaturated fatty acid) in accordance with one aspect of the present invention.

Two of the Rpf proteins, RpfB and RpfF, work to produce a diffusible signal factor (DSF) which has recently been described as an alpha,beta unsaturated fatty acid having the structure shown in FIG. 6. Wang, Lian-Hui, He, Y., Gao, Y., Wu, J. E., Dong, Y.-H., He, C., Wang, S. X., Weng, L.-X., Xu, J.-L., Tay, L., Fang, and R. X., Zhang, L.-H. 2004. Cell-cell communication signal with cross-kingdom structural analogues. Molecular Microbiology. 51: 903-912. As noted above, as the population grows, the local concentration of DSF increases. Other Rpf proteins are thought to sense the increase in DSF concentration and transduce a signal, resulting in expression of pathogenicity factors. Slater, H., A. Alvarez-Morales, C. E. Barber, M. J. Daniels, and J. M. Dow. 2000. A two-component system involving an HD-GYP domain protein links cell-cell signaling to pathogenicity gene expression in *Xanthomonas campestris*. Molecular Microbiology 38:986-1003. It has been found that several other bacterial species can both positively and negatively interact with the DSF-mediated cell-cell signaling in Xf, but the manner in which the interaction occurred nor whether such strains had the potential to affect the virulence of Xf in grape was not previously known. In this study, the role of DSF-production by Xf on its behavior within plants and insects as well as the manner in which other bacterial strains affect such cell signaling has been extensively investigated, and the extent to which other endophytes could modulate density-dependent behaviors and virulence in Xf by interfering with cell-cell signaling has been determined.

Results

Figure 7:
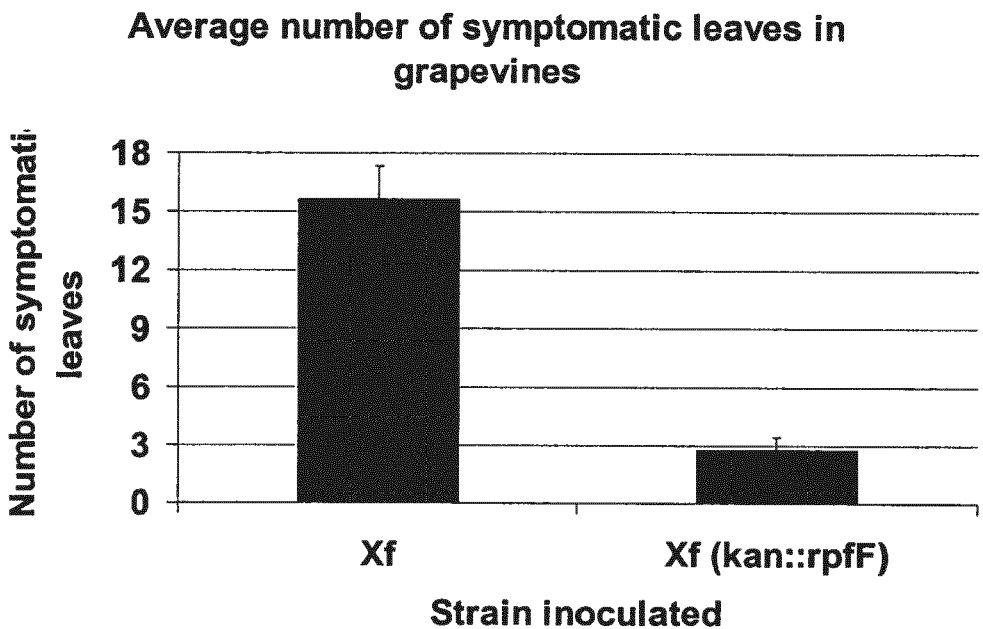
FIGS. 7 and 8 illustrate the results of an experiment showing that the severity of Pierce's disease in plants was greatly reduced when rpfF was over-expressed in Xf under the control of a high and constitutive promoter in accordance with one aspect of the present invention.
Figure 8:
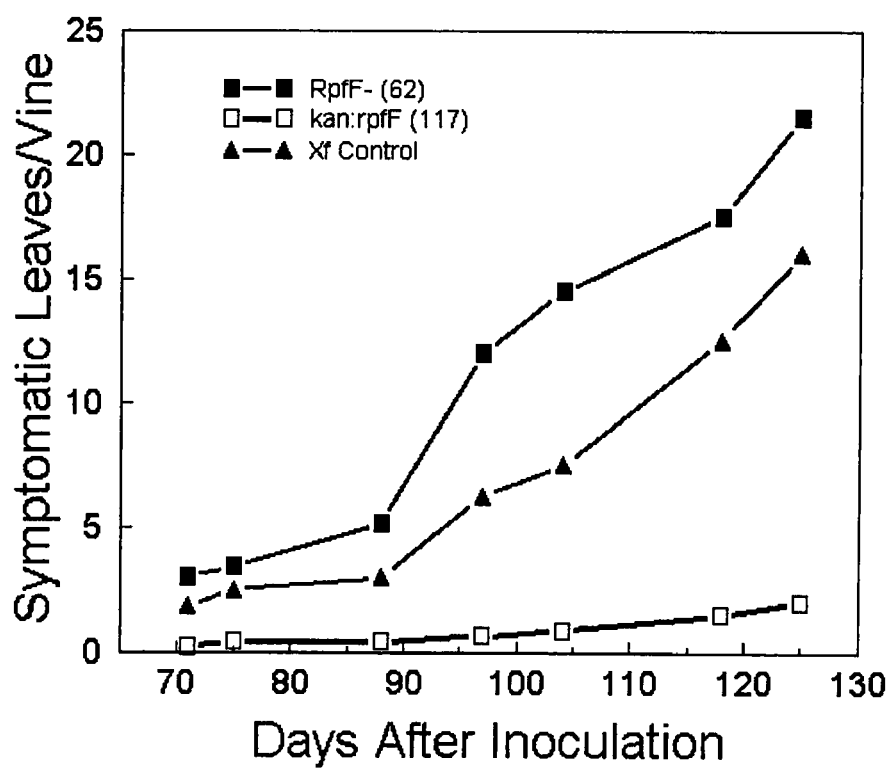
Figure 9:
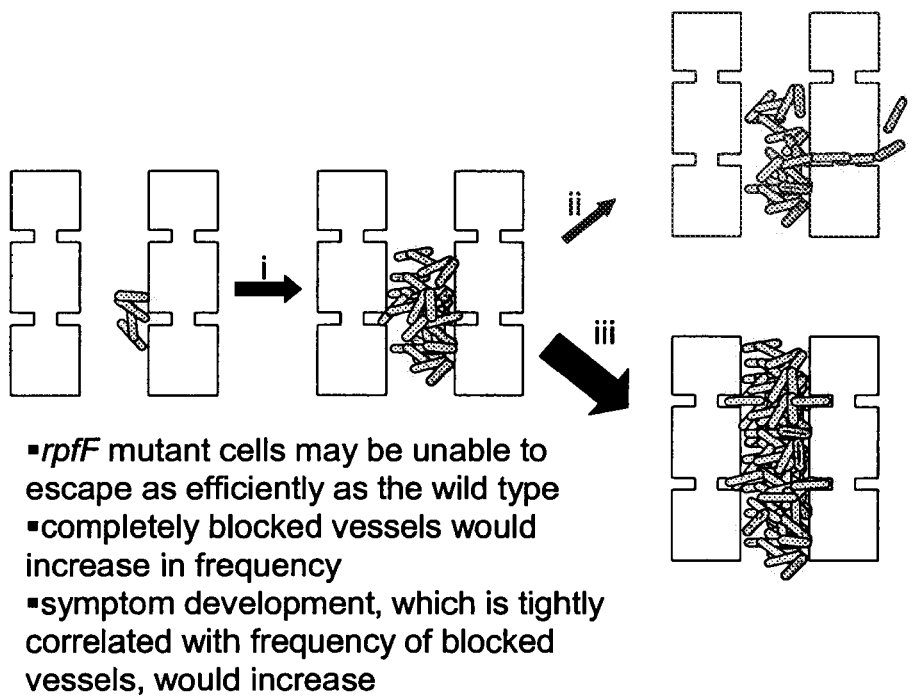
FIG. 9 illustrates a model of DSF regulation of genes required for movement of Xf from colonized vessels.

A strain of Xf Temecula was constructed in which the rpfF gene, which is required for production of the signal in Xcc, is knocked out. This mutant was constructed using exchange of the wild-type allele for a deleted copy carrying an antibiotic resistance gene on a suicide plasmid. The rpfF mutant of Xf does not make DSF as determined using previously constructed "signal-sensing" strains of Xcc to determine DSF production by Xf and other bacterial strains. rpfF mutant strains were tested for their ability to infect and move within host plants and to cause Pierce's disease symptoms. The rpfF gene appears to play a role in modulating disease progress because the timing and severity of symptom development are greatly exacerbated in grapevines infected with rpfF mutants when compared to the wild type. The mechanism behind these differences has been investigated. No detectable difference in populations or movement between the wild type and rpfF mutants has been found, although the sampling methods used would not be able to detect small increases in colonization if they existed. As noted previously, it is hypothesized that rpfF mutants may be causing increased vessel blockage in the grapevine, leading to increased symptom expression. A green fluorescent rpfF mutant was made to investigate the pattern of colonization by the mutant and compare it to that of the wild type. Importantly, when rpfF was over-expressed in Xf under the control of a high and constitutive promoter, the severity of disease in plants was greatly reduced, as illustrated in FIGS. 7 and 8. The Xf strain that overproduced DSF caused disease symptoms in grape, but only at the site of inoculation. The mutant cells did not move within the plant as did wild-type strains. These results all support a model, illustrated in FIG. 9, that DSF regulates genes required for movement of Xf from colonized vessels. Such results suggest that elevating DSF levels in plants should reduce movement of Xf in the plant.

Figure 10:
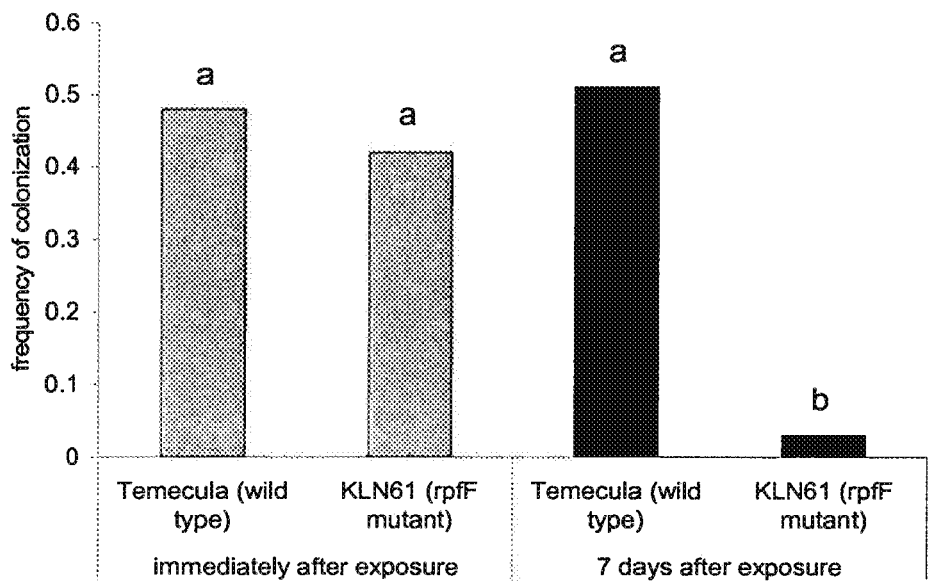
FIG. 10 illustrates the experimental result that leafhoppers fed on rpfF mutant-infected plants ingested rpfF cells but were able to rapidly clear themselves whereas the wild type is never cleared.

The transmissibility of the rpfF mutant strain by an insect vector was also tested. The rpfF mutant was virtually untransmissible. This defect in transmissibility by the signaling-deficient mutant reveals the importance of cell-cell signaling in insect transmission. Leafhoppers fed on rpfF mutant-infected plants ingested rpfF cells but were able to rapidly clear themselves whereas the wild type is never cleared as illustrated in FIG. 10.

In addition, a variety of bacteria were isolated from grapevines from vineyards affected by Pierce's disease as well as tomato and cruciferous crop plants infected with the signal-producing pathogens *Xanthomonas campestris* pv. *vessicatoria* and Xcc, respectively and tested for their ability to interfere with cell-cell signaling in Xf in an assay using the signal-sensing strain described above. Several strains that negatively affected signaling in Xcc were found while several strains were found to produce DSF. By adding purified DSF to either cell-free extracts of the strains with a negative influence on signaling or to whole cells it was found that at least two mechanisms of interference with signaling could be observed. Some strains such as strains C, E, G, H, and J are able to degrade DSF while other inhibitor strains did not do so, and apparently have another means of interfering with DSF perception by Xcc. The several strains that produced DSF were all identified as *Xanthomonas* species. The 16S rRNA gene from these strains was sequenced to determine their species identity (noted in the Table 1, below):

TABLE 1

| Strain | Genus | Origin | Mechanism of DSF Interference |
|---|---|---|---|
| A | *Paenibacillus* | Grape | Unknown inhibition |
| B | *Paenibacillus* | Grape | Unknown inhibition |
| C | *Pseudomonas* | Cabbage | Enzymatic digestion |
| D | *Staphylococcus* | Grape | Unknown inhibition |
| E | *Bacillus* | Broccoli | Enzymatic digestion |
| G | *Pseudomonas* | Cabbage | Enzymatic digestion |
| H | *Pseudomonas* | Cabbage | Enzymatic digestion |
| J | *Pseudomonas* | Tomato | Enzymatic digestion |
| L | *Staphylococcus* | Grape | Unknown inhibition |
| I | *Xanthomonas* | Tomato | DSF production |
| U | *Xanthomonas* | Broccoli | DSF production |
| V | *Xanthomonas* | Broccoli | DSF production |
| W | *Xanthomonas* | Broccoli | DSF production |
| X | *Xanthomonas* | Broccoli | DSF production |
| Y | *Xanthomonas* | Tomato | DSF production |
| Z | *Xanthomonas* | Grape | DSF production |

To verify that disease control is due to DSF interference, mutants of bacterial strains that disrupt the ability of these strains to produce or degrade DSF were constructed and it has been shown that these mutants are deficient in Pierce's disease (PD) control. Both mutants unable to produce DSF as well as mutants deficient in degradation of DSF exhibited less ability to control PD when coinoculated with Xf, suggesting that altering DSF abundance within the plant was a major factor contributing to disease control by these DSF-interfering strains.

Given that DSF overabundance appears to mediate an attenuation of virulence in Xf grape has been transformed with the rpfF gene of Xf to enable DSF production in planta. Preliminary results indicate that transient expression of rpfF in *Nicotiana benthamiana* following infiltration with appropriate *Agrobacterium tumefaciens* strains resulted in high levels of DSF production, suggesting that grape cells will produce DSF when transformed with the bacterial rpfF gene. The bacterial genes required for DSF degradation have been cloned and identified in antagonist strain G, enabling their exploitation for disease control by both over-expression in various bacterial endophytes of grape as well as by expression within plants themselves. Non-endophytic bacterial species were also established in high numbers inside grape leaves and petioles following spray application to plants with a high concentration of a silicon-based surfactant with a low surface tension, suggesting the possibility of producing protective compounds such as DSF in plants using a variety of bacteria.

Figure 11:
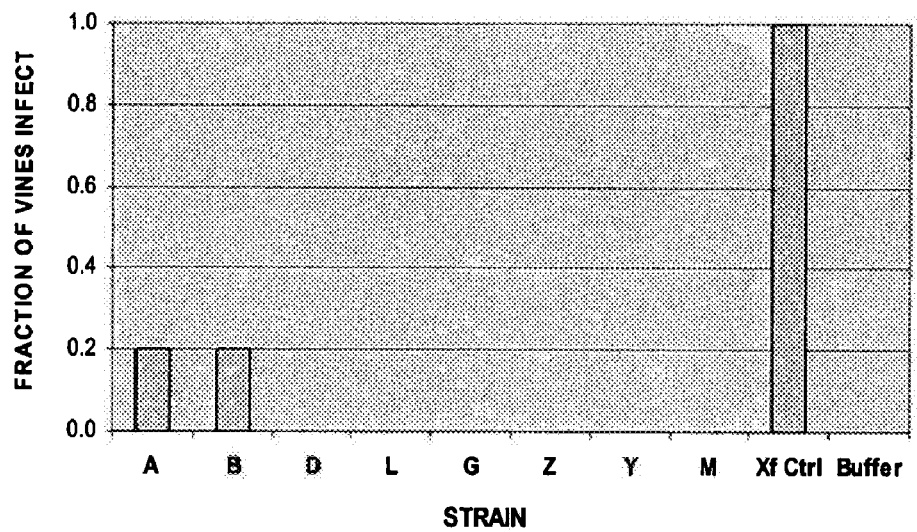
FIG. 11 illustrates that the incidence of Pierce's disease was greatly reduced by all of the DSF-interfering strains that were tested in accordance with one aspect of the present invention.

As noted above, to test the ability of bacteria that alter Xf signaling to alter the process of disease in plants, grapevines with Xf and strains that either inhibit or activate cell-cell signaling were co-inoculated in greenhouse studies. The incidence of Pierce's disease was greatly reduced by all of the signaling interfering strains that were tested, as illustrated in FIGS. 4 and 11. DSF-producing strains generally reduced disease severity more than did strains that interfered with signaling in Xf (FIG. 3). These results were highly repeatable and indicate that alteration of signal molecules within plants can have a profound effect on the disease process.

Figure 12:
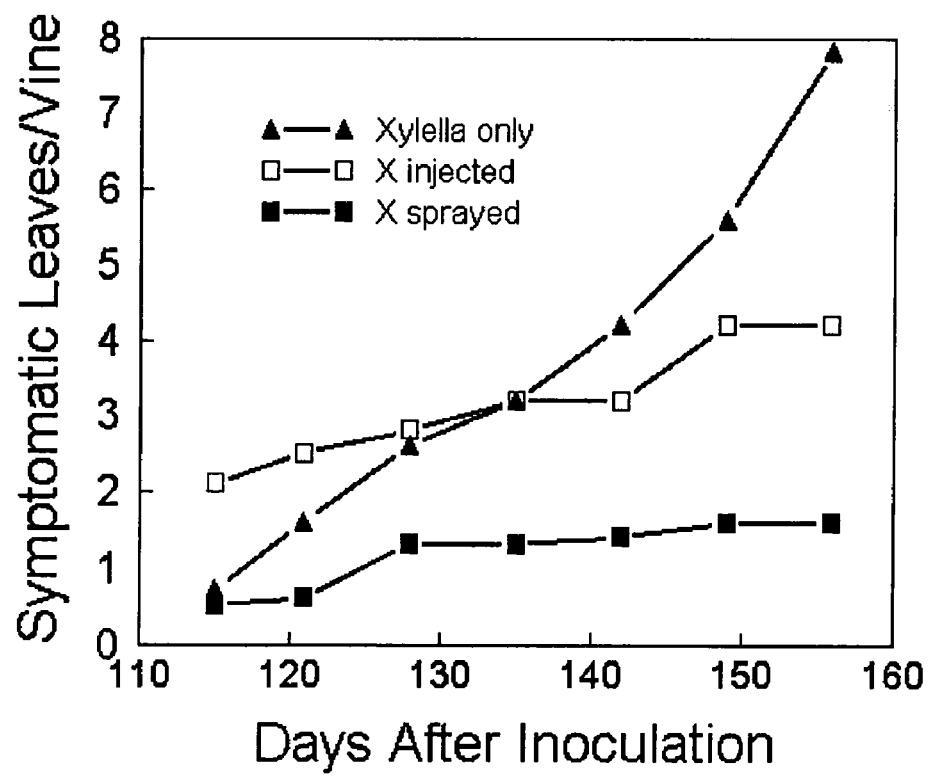
FIG. 12 illustrates disease control by topical inoculation of DSF-producing bacteria to the foliage of plants as well as by pre-treatment of plants by injection before inoculation with Xf in accordance with one aspect of the present invention.

Disease control by topical inoculation has also been demonstrated. The results of inoculation of DSF-producing bacteria, such as DSF-producing strains X and 8004, to the foliage of plants where they colonize and presumably produce DSF as well as by pre-treatment of plants by injection of these antagonists before inoculation with Xf, are illustrated in FIG. 12.

Figure 13:
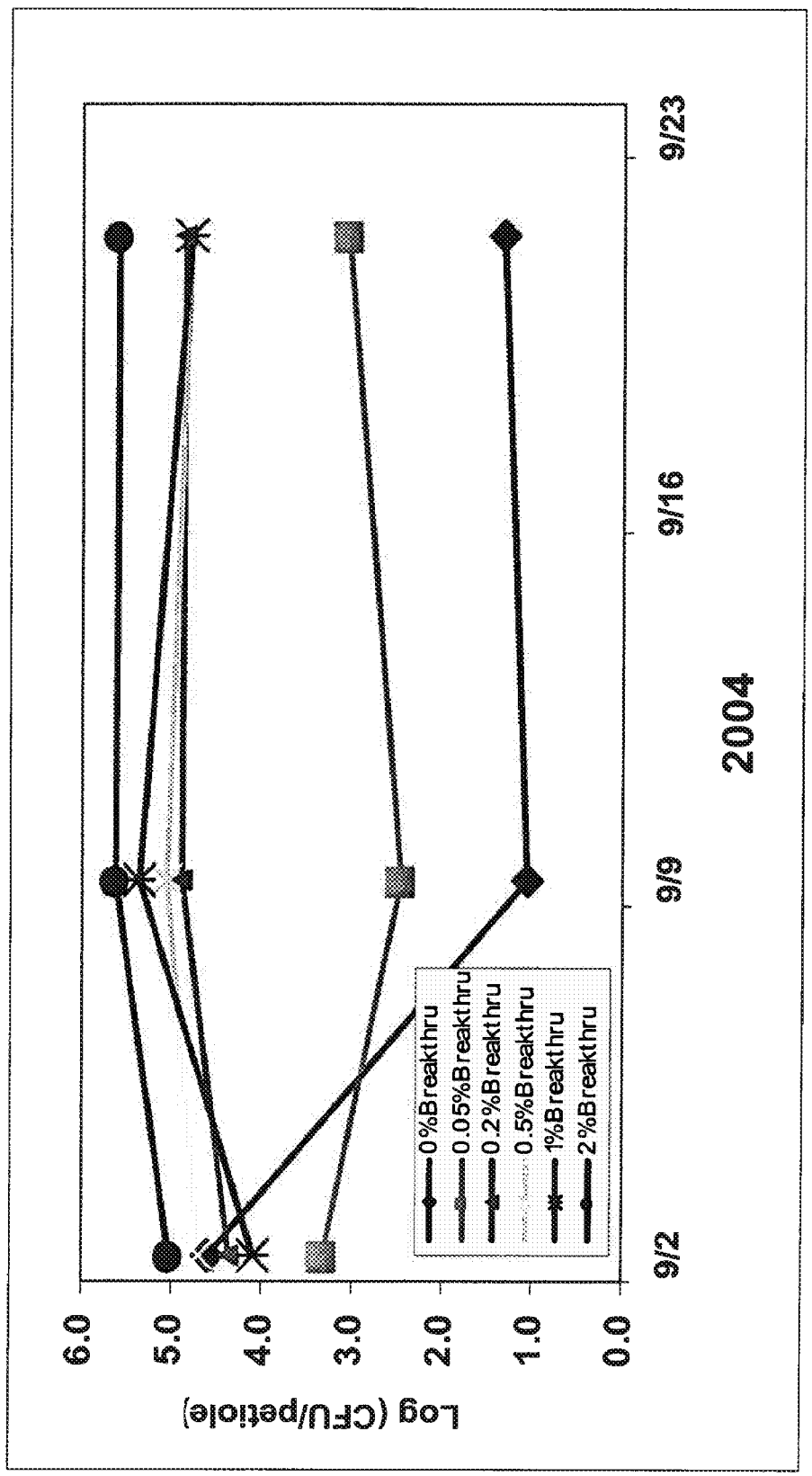
FIG. 13 illustrates the results of topical applications of bacterial suspensions to plants in solutions of organosilicone surfactants having very low surface tensions in accordance with one aspect of the present invention.

It has also been found that it is possible to establish large populations of bacteria within grape leaves, stems and petioles by simple topical applications of bacterial suspensions to plants in solutions of organosilicone surfactants having very low surface tensions. Non-endophytic bacterial species were also established in high numbers inside grape leaves and petioles following spray application to plants with a high concentration (e.g., about 0.2 to 1.0% V/V, for example about 0.5% to 1.0%) of a silicon-based surfactant with a low surface tension (e.g., less than 25 dynes/cm), such as the product Break-Thru®, available from Goldschmidt Chemical Corporation, suggesting that it may be possible to produce protective compounds such as DSF in plants by a variety of bacteria. Bacteria were found to colonize grape for at very high population sizes (e.g., greater than $10^6$ cells/petiole) for extended periods of time following topical application (FIG. 13). While these bacteria apparently do not spread throughout the plant after inoculation as does Xf, by introducing it into the intercellular spaces and perhaps even the xylem of the plant by use of the surfactants that stimulate spontaneous infiltration of the plant, the bacteria can be inoculated into all sites within the plant. Such non-pathogenic bacteria then increased in population size after inoculation, apparently by growing locally where they had been inoculated. This finding suggests exploiting a variety of DSF-interfering bacteria for practical control of PD. Such bacteria could produce large amounts of DSF after introduction into the plant. The observation that large numbers of bacteria can be introduced into grape plants by simple topical applications of cell suspensions in a penetrating surfactant provides an additional disease control strategy that should prove practical for commercial use.

To establish a rigorous connection between DSF production and disease control, mutant strains have been constructed of those DSF-producing bacteria that perform best in the disease control assays described above that no longer could produce DSF. These mutants were then compared to their parent strains in the disease control assays. Mutants of DSF-degrading strains that no longer could degrade DSF were also made. As illustrated in FIGS. 14-16, all mutants unable to produce DSF were diminished in ability to reduce PD when co-inoculated with Xf compared to their DSF-producing wild-type strain, many dramatically so.

Likewise, as illustrated in FIG. 17, mutant strain G741, a mutant of DSF-degrading parental strain G that no longer could degrade DSF also was greatly reduced in ability to control PD when co-inoculated with Xf compared to its parental strain. These results suggest strongly that it is the production of, or degradation of DSF in plants by these antagonistic bacteria that makes a large contribution to their ability to reduce PD. The results thus strongly suggest that any method that either increases or decreases DSF abundance in Xf-infected plants will have a large effect on the incidence and/or severity of Pierce's disease.

To increase the usefulness of any interfering agents identified in this screen, genes conferring the DSF-interference phenotypes can be molecularly identified. This gene can then be introduced into other organisms, such as plants.

Interfering strain G, typical of strains that apparently degrade DSF, was subjected to transposon mutational analysis of the interfering activity. Several insertional mutations that block degradation of DSF were identified. The genes have been inactivated individually by random Tn5 mutagenesis and cloned the disrupted loci. A library of mutants of strain G was obtained by mating strains with pRL27, a suicide vector carrying a Tn5-derivative transposon. Larsen, R. A., Wilson, M. M., Guss, A. M. & Metcalf, W. W. Genetic analysis of pigment biosynthesis in *Xanthobacter autotrophicus* Py2 using a new, highly efficient transposon mutagenesis system that is functional in a wide variety of bacteria. *Arch Microbiol* 178, 193-201 (2002). Transposon insertion events conferred kanamycin resistance to the host cells, allowing efficient selection of mutated cells. The resulting mutant collections were screened for a loss of the ability to interfere with DSF signaling using the DSF biosensor-based screen described above. Mutations of the carAB genes, encoding carbamoyl-phosphate synthetase activity, in antagonist G abolish DSF degradation. Multiple mutants of these two genes have been found to disrupt DSF production:

Genbank Accession No. NC_007005 (gi:66043271) (SEQ ID NO:5 and SEQ ID NO:6, respectively)

```
carA:
translation = "MTKPAILALADGSIFRGEAIGADGQTVGEVVFNTA
MTGYQEILTDPSYAQQIVTLTYPHIGNTGTTPEDAESDRVWSAGLVIRDL
PLVASNWRNKLSLGDYLKANNVVAIAGIDTRRLTRILREKGAQNGCILAG
DNITEEAAIAAARGFPGLKGMDLAKEVCTKDTYEWRSSVWDLKTDSHPEI
AASELPYHVVAYDYGVKVNILRMLVERGCRVTVVPAQTPASEVLAYKPDG
VFLSNGPGDPEPCDYAIKAIREVLETDIPVFGICLGHQLLALAAGAKTVK
MGHGHHGANHPVQDLDTGVVMITSQNHGFAVDEATLPSNVRAIHKSLFDG
TLQGIELTDKSAFSFQGHPEASPGPNDVAPLFDRFIEAMAKRR"

carB:
translation = "MPKRTDIKSILILGAGPIVIGQACEFDYSGAQACK
ALREEGYRVILVNSNPATIMTDPAMADATYIEPIKWQTVAKIIEKERPDA
LLPTMGGQTALNCALDLEREGVLEKFGVEMIGANADTIDKAEDRSRFDKA
MKSIGLACPRSGIAHSMEEANAVLEKLGFPCIIRPSFTMGGTGGGIAYNR
EEFEEICARGLDLSPTKELLIDESLIGWKEYEMEVVRDKKDNCIIVCSIE
NFDPMGVHTGDSITVAPAQTLTDKEYQILRNASLAVLREIGVETGGSNVQ
FGICPNTGRMVVIEMNPRVSRSSALASKATGFPIARVAAKLAVGYTLDEL
SNEITGGKTPASFEPSIDYVVTKLPRFAFEKFAKADARLTTQMKSVGEVM
AIGRTFQESLQKALRGLEVGVCGLDPKLDLSHPESMSTLKRELTVPGAER
IWYVADAFRAGMTVEEIFAMNMIDPWFLVQIEDLIKDEEKIKTLGLSAID
RDVMFRLKRKGFSDARLAKLLGVTEKNLRTHRHKLEVFPVYKRVDTCAAE
FATDTAYLYSTYEEECEANPSTRDKIMILGGGPNRIGQGIEFDYCCVHAA
LALREDGYETIMVNCNPETVSTDYDTSDRLYFEPVTLEDVLEIVRVEKPK
GVIVQYGGQTPLKLARALEAAGVPIIGTSPDAIDRAEDRERFQHMVERLN
LRQPPNATVRSEDEAIRAAAKIGYPLVVRPSYVLGGRAMEIVYQEDELKR
YLREAVQVSNDSPVLLDHFLNCAIEMDVDAVCDGTDVVIGAIMQHIEQAG
VHSGDSACSLPPYSLPAHIQDEMREQVKKMALELGVVGLMNVQLALQGED
IYVIEVNPRASRTVPFVSKCIGVSLAMIAARVMAGKTLKELNFTKEIIPN
FYSVKEAVFPFAKFPGVDPILGPEMKSTGEVMGVGDTFGEAFAKAQMGAS
EVLPTGGTAFISVRDDDKPLVEAVARDLINLGFEIVATAGTAKLIEAAGL
KVRRVNKVTEGRPHVVDMIKNDEVTLIINTTEGRQSIADSYSIRRNALQH
KIYCTTTIAAGEAICEALKFGPEKTVRRLQDLHAGLKA"
```

The enzyme's mechanism of DSF degradation can be investigated by over-expressing it. The genetics of DSF degradation in this and other strains can be explored using this mutagenesis strategy or by constructing cosmid libraries in pLAFR3 (Huynh, T. V., Dahlbeck, D. & Staskawicz, B. J.

Bacterial Blight of Soybean Regulation of a Pathogen Gene Determining Host Cultivar Specificity. Science 245, 1374-1376 (1989)) and screening for the ability to degrade DSF or interfere with signaling when introduced into *E. coli*, or if necessary Xcc, using the DSF biosensor strategy described above with reference to FIGS. 1 and 2. The location of genes can be determined by standard subcloning and insertional mutagenesis approaches, and the identity of the genes revealed by sequencing of subcloned fragments.

Disease control by DSF-interfering strains can be optimized if they are good colonists of grapevine. To maximize disease control the various genes conferring DSF interference can be expressed in effective non-pathogenic endophytic colonists of grapevine such as *Alcaligenes xylosoxidans denitrificans* (Axd) and *Agrobacterium vitis* (Av). This strategy should deliver the disease control agent directly to the site of the pathogen and result in highly effective control. Since the rpfF gene of Xf is sufficient to confer expression of DSF in other bacteria, it is being introduced into these two species. For Axd, technology developed in the laboratory of Dr. David Lampe, which employs a transposon-containing plasmid, pSP14, to deliver genes directly into the chromosome of Axd can be used (Bextine, B. R., Lauzon, C. R., Potter, S. E., Lampe, D. & Miller, T. E. Delivery of a genetically marked *Alcaligenes* sp. to the glassy-winged sharpshooter for use in a paratransgenic control strategy. *Current Microbiology* 48, 327-31 (2004). Both DSF-activating and DSF-inhibiting genes under the control of the constitutive Kan promoter can be transferred from Tn903 into Axd. The DSF degradation genes can introduced into Av on the stable vector pVSP61.

DSF degradation reduces pathogenicity of Xcc and virulence of Xf. Black rot symptoms in mustard are reduced when strain G is co-inoculated with the pathogen, however this reduction in symptom severity is not seen when strain G741, a Tn5 mutant that can no longer degrade DSF, is co-inoculated (FIG. 18). Pierce's disease occurrence in grapevines is reduced in frequency when strain G is co-inoculated with the pathogen (FIG. 19). The gene mutated in strain G741 as well as the other four mutants was the carAB locus, cited above. This indicates that the carAB locus encodes a DSF-degradation activity. Therefore, the carAB-encoded enzyme is an example of a DSF-degrading enzyme that can be used to degrade DSF.

Discussion of Example Results

Substantial data show that cell-cell signaling plays a major role in the epidemiology and virulence of Xf and that disruption of cell signaling is a promising means of controlling Pierce's disease and other DSF-mediated plant diseases. Strikingly, Xf strains that cannot signal are also not transmissible by nor colonize an efficient insect vector. This result reveals an important and previously unappreciated connection between cell-cell signaling and transmission as well as the requirement for biofilm formation for transmission. These findings provide a basis for a transmission-mediated disease control strategy.

The findings that mutants unable to signal are hypervirulent, but that strains of Xf that overproduce DSF have low virulence and do not move within grape indicated that value of the elucidation of Xf's colonization strategies rather than traits predicted to contribute to virulence based on studies of other plant pathogens. Bacterial strains have been identified that can interfere with Xf signaling. These strains proved very effective as protective agents for grapevines when co-inoculated with Xf. Both positive and negative interference with DSF signaling reduced disease in grape suggesting that signaling is normally finely balanced in the disease process; such a finely balanced process might be readily disrupted. Since in bacteria rpfF is sufficient to encode a synthase capable of DSF production, expression of DSF directly in plants is a attractive approach for disease control. Preliminary results are very encouraging that DSF can be made in plants. Alternatively, the use of various bacteria to express DSF in plants may prove equally effective in altering Xf behavior and hence disease control. And, the observation that large numbers of bacteria can be introduced into grape plants by simple topical applications of cell suspensions in a penetrating surfactant provides an additional disease control strategy that should prove practical for commercial use.

CONCLUSION

Agricultural diseases caused by DSF-producing pathogens can be controlled by blocking cell-cell signaling in organisms susceptible to these pathogens. Blocking cell-cell DSF signaling reduces virulence (in the case of the *Xanthomonads*) or spread (in the case of *Xylella*) of the pathogen.

The control may be by several potential methods: 1) by using a DSF-interference (inhibitor or activator) strain as a biocontrol agent; 2) by expressing a DSF-interference gene (degrader, analog, or synthase) in an effective endophytic or epiphytic colonist of the plant; or, 3) by expressing a DSF-interference gene in the plant or rootstock.

While the invention has been primarily described herein with reference to bacterial diseases or plants, some of these methods could also be useful for control of fungi, since some fungal pheromones are structurally related to DSF. In addition, several human pathogens express DSF and may use this signal to control pathogenicity. Therefore, the DSF-interference-based control strategies described herein may have application for control of non-bacterial and/or non-plant pathogens.

Although the foregoing invention has been described in some detail for purposes of clarity of understanding, it will be apparent that certain changes and modifications may be practiced within the scope of the appended claims. It should be noted that there are many alternative ways of implementing both the process and compositions of the present invention. Accordingly, the present embodiments are to be considered as illustrative and not restrictive, and the invention is not to be limited to the details given herein.

All references cited herein are incorporated by reference in their entirety for all purposes.

It is claimed:

1. A transgenic plant cell, the cell comprising:

a promoter active in plant cells, wherein the promoter is operatively linked to a coding sequence of a bacterial rpf gene that encodes a protein that participates in the production of microbial α,β unsaturated fatty acid signal molecules, wherein the rpf gene is from a bacterium of the genus *Xanthomonas* or *Xylella*, and wherein the rpf gene encodes RpfB protein or RpfF protein.

2. The transgenic plant cell of claim 1, wherein the plant cell is selected from the group consisting of a genus Brassicaceae cell, a genus Solanaceae cell, a rice cell and a grape cell.

3. The transgenic plant cell of claim 1, wherein the rpf gene is from a bacterium of the genus *Xanthomonas.*

4. The transgenic plant cell of claim 3, wherein the bacterium is *X. campestris* pathovar *campestris* (Xcc), and the plant cell is a Brassicacea cell.

5. The transgenic plant cell of claim 3, wherein the bacterium is *X. campestris* pathovar *vesicatoria* (Xcv), and the plant cell is a Solanaceae cell.

6. The transgenic plant cell of claim 3, wherein the bacterium is *X. oryzae* pathovar *oryzae* (Xoo), and the plant cell is a rice cell.

7. The transgenic plant cell of claim 1, wherein the rpf gene is from a bacterium of the genus *Xylella.*

8. The transgenic plant cell of claim 7, wherein the bacterium is *X. fastidiosa* (XJ), and the plant cell is a grape cell.

9. The transgenic plant cell of claim 1, wherein the rpf gene encodes RpfB protein.

10. The transgenic plant cell of claim 1, wherein the rpf gene encodes RpfF protein.

11. The transgenic plant cell of claim 10, wherein the rpf gene encodes Xf RpfF.

12. The transgenic plant cell of claim 11, wherein the rpf gene encodes SEQ ID NO:1.

13. The transgenic plant cell of claim 10, wherein the rpf gene encodes Xcc RpfF.

14. The transgenic plant cell of claim 13, wherein the rpf gene encodes SEQ ID NO:2.

15. The transgenic plant cell of claim 1, wherein the promoter comprises a constitutive plant promoter.

16. The transgenic plant cell of claim 1 wherein the promoter is selected from the group consisting of the cauliflower mosaic virus 35S promoter and the ubiquitin promoter.

17. A transgenic plant comprising cells according to claim 1.

18. A transgenic plant cell, the cell comprising:

a promoter active in plant cells, wherein the promoter is operatively linked to a coding sequence of a bacterial carA gene or carB gene.

19. The transgenic plant cell of claim 18, wherein the promoter is operatively linked to a coding sequence of a bacterial carA gene.

20. The transgenic plant cell of claim 19, where the carA gene encodes SEQ ID NO:5.

21. The transgenic plant cell of claim 18, wherein the promoter is operatively linked to a coding sequence of a bacterial carB gene.

22. The transgenic plant cell of claim 21, where the carB gene encodes SEQ ID NO:6.

23. A transgenic plant comprising cells according to claim 18.

* * * * *

SEQUENCE LISTING

<160> NUMBER OF SEQ ID NOS: 6

<210> SEQ ID NO 1
<211> LENGTH: 290
<212> TYPE: PRT

-continued

<213> ORGANISM: Xylella fastidiosa

<400> SEQUENCE: 1

Met Ser Ala Val His Pro Ile Pro His Pro Ile Cys Glu Ser Ser Ile
1               5                   10                  15

Arg Ile Ile Glu Glu Thr His Arg Asn Val Tyr Trp Ile Tyr Met His
            20                  25                  30

Ala His Leu Ala Arg Thr Thr Gly Ala Ala Tyr Phe Ser Leu Lys Leu
        35                  40                  45

Ile Asp Asp Ile Met Asn Tyr Gln Ser Val Leu Arg Gln Arg Leu Lys
    50                  55                  60

Glu Gln Thr Val Gln Leu Pro Phe Val Val Leu Ala Ser Asp Ser Asn
65                  70                  75                  80

Val Phe Asn Leu Gly Gly Asp Leu Gln Leu Phe Cys Asp Leu Ile Arg
                85                  90                  95

Arg Lys Glu Arg Glu Ala Leu Leu Asp Tyr Ala Cys Arg Cys Val Arg
            100                 105                 110

Gly Ala Tyr Ala Phe His Ala Gly Leu Asn Ala Asn Val His Ser Ile
        115                 120                 125

Ala Leu Leu Gln Gly Asn Ala Leu Gly Gly Phe Glu Ala Ala Leu
    130                 135                 140

Cys Cys His Thr Ile Val Ala Glu Glu Gly Val Met Met Gly Phe Pro
145                 150                 155                 160

Glu Val Leu Phe Asp Leu Phe Pro Gly Met Gly Ala Tyr Ser Phe Met
                165                 170                 175

Arg Gln Arg Ile Ser Pro Lys Leu Ala Glu Arg Leu Ile Leu Glu Gly
            180                 185                 190

Asn Leu Tyr Ser Ser Glu Glu Leu Leu Ala Ile Gly Leu Ile Asp Lys
        195                 200                 205

Val Val Pro Arg Gly Lys Gly Ile Glu Ala Val Glu Gln Ile Ile Arg
    210                 215                 220

Asp Ser Lys Arg Arg Gln Tyr Thr Trp Ala Ala Met Gln Glu Val Lys
225                 230                 235                 240

Lys Ile Ala His Glu Val Ser Leu Glu Glu Met Ile Arg Ile Thr Glu
                245                 250                 255

Leu Trp Val Asp Ser Ala Leu Lys Leu Ser Asn Lys Ser Leu Arg Thr
            260                 265                 270

Met Glu Arg Leu Ile Arg Ala Gln Gln Thr His Lys Asn Thr Ala Leu
        275                 280                 285

Lys Asn
    290

<210> SEQ ID NO 2
<211> LENGTH: 289
<212> TYPE: PRT
<213> ORGANISM: Xanthomonas campestris

<400> SEQUENCE: 2

Met Ser Ala Val Gln Pro Phe Ile Arg Thr Asn Ile Gly Ser Thr Leu
1               5                   10                  15

Arg Ile Ile Glu Glu Pro Gln Arg Asp Val Tyr Trp Ile His Met His
            20                  25                  30

Ala Asp Leu Ala Ile Asn Pro Gly Arg Ala Cys Phe Ser Thr Arg Leu
        35                  40                  45

Val Asp Asp Ile Thr Gly Tyr Gln Thr Asn Leu Gly Gln Arg Leu Asn
    50                  55                  60

Thr Ala Gly Val Leu Ala Pro His Val Leu Ala Ser Asp Ser Asp
 65                  70                  75                  80

Val Phe Asn Leu Gly Gly Asp Leu Ala Leu Phe Cys Gln Leu Ile Arg
                 85                  90                  95

Glu Gly Asp Arg Ala Arg Leu Leu Asp Tyr Ala Gln Arg Cys Val Arg
            100                 105                 110

Gly Val His Ala Phe His Val Gly Leu Gly Ala Arg Ala His Ser Ile
        115                 120                 125

Ala Leu Val Gln Gly Asn Ala Leu Gly Gly Gly Phe Glu Ala Ala Leu
    130                 135                 140

Ser Cys His Thr Ile Ile Ala Glu Glu Gly Val Met Met Gly Leu Pro
145                 150                 155                 160

Glu Val Leu Phe Asp Leu Phe Pro Gly Met Gly Ala Tyr Ser Phe Met
                165                 170                 175

Cys Gln Arg Ile Ser Ala His Leu Ala Gln Lys Ile Met Leu Glu Gly
            180                 185                 190

Asn Leu Tyr Ser Ala Glu Gln Leu Leu Gly Met Gly Leu Val Asp Arg
        195                 200                 205

Val Val Pro Arg Gly Gln Gly Val Ala Val Glu Gln Val Ile Arg
    210                 215                 220

Glu Ser Lys Arg Thr Pro His Ala Trp Ala Ala Met Gln Gln Val Arg
225                 230                 235                 240

Glu Met Thr Thr Ala Val Pro Leu Glu Glu Met Met Arg Ile Thr Glu
                245                 250                 255

Ile Trp Val Asp Thr Ala Met Gln Leu Gly Glu Lys Ser Leu Arg Thr
            260                 265                 270

Met Asp Arg Leu Val Arg Ala Gln Ser Arg Ser Gly Leu Asp Ala
        275                 280                 285

Gly

<210> SEQ ID NO 3
<211> LENGTH: 38
<212> TYPE: DNA
<213> ORGANISM: Artificial Sequence
<220> FEATURE:
<223> OTHER INFORMATION: Xf rpfF F Nco I primer

<400> SEQUENCE: 3
taccatggcc gctgtacatc ccattcctca ccccatat                      38

<210> SEQ ID NO 4
<211> LENGTH: 40
<212> TYPE: DNA
<213> ORGANISM: Artificial Sequence
<220> FEATURE:
<223> OTHER INFORMATION: Xf rpfF R Bam HI primer

<400> SEQUENCE: 4
cgggatcctc agtttttag tgctgtgttt ttgtgagtct                      40

<210> SEQ ID NO 5
<211> LENGTH: 378
<212> TYPE: PRT
<213> ORGANISM: Pseudomonas syringae

<400> SEQUENCE: 5

Met Thr Lys Pro Ala Ile Leu Ala Leu Ala Asp Gly Ser Ile Phe Arg
  1               5                  10                  15

-continued

Gly Glu Ala Ile Gly Ala Asp Gly Gln Thr Val Gly Glu Val Val Phe
         20                  25                  30

Asn Thr Ala Met Thr Gly Tyr Gln Glu Ile Leu Thr Asp Pro Ser Tyr
             35                  40                  45

Ala Gln Gln Ile Val Thr Leu Thr Tyr Pro His Ile Gly Asn Thr Gly
 50                  55                  60

Thr Thr Pro Glu Asp Ala Glu Ser Asp Arg Val Trp Ser Ala Gly Leu
 65                  70                  75                  80

Val Ile Arg Asp Leu Pro Leu Val Ala Ser Asn Trp Arg Asn Lys Leu
                 85                  90                  95

Ser Leu Gly Asp Tyr Leu Lys Ala Asn Asn Val Val Ala Ile Ala Gly
            100                 105                 110

Ile Asp Thr Arg Arg Leu Thr Arg Ile Leu Arg Glu Lys Gly Ala Gln
            115                 120                 125

Asn Gly Cys Ile Leu Ala Gly Asp Asn Ile Thr Glu Glu Ala Ala Ile
130                 135                 140

Ala Ala Ala Arg Gly Phe Pro Gly Leu Lys Gly Met Asp Leu Ala Lys
145                 150                 155                 160

Glu Val Cys Thr Lys Asp Thr Tyr Glu Trp Arg Ser Ser Val Trp Asp
                165                 170                 175

Leu Lys Thr Asp Ser His Pro Glu Ile Ala Ala Ser Glu Leu Pro Tyr
            180                 185                 190

His Val Ala Tyr Asp Tyr Gly Val Lys Val Asn Ile Leu Arg Met
            195                 200                 205

Leu Val Glu Arg Gly Cys Arg Val Thr Val Val Pro Ala Gln Thr Pro
210                 215                 220

Ala Ser Glu Val Leu Ala Tyr Lys Pro Asp Gly Val Phe Leu Ser Asn
225                 230                 235                 240

Gly Pro Gly Asp Pro Glu Pro Cys Asp Tyr Ala Ile Lys Ala Ile Arg
                245                 250                 255

Glu Val Leu Glu Thr Asp Ile Pro Val Phe Gly Ile Cys Leu Gly His
            260                 265                 270

Gln Leu Leu Ala Leu Ala Ala Gly Ala Lys Thr Val Lys Met Gly His
            275                 280                 285

Gly His His Gly Ala Asn His Pro Val Gln Asp Leu Asp Thr Gly Val
290                 295                 300

Val Met Ile Thr Ser Gln Asn His Gly Phe Ala Val Asp Glu Ala Thr
305                 310                 315                 320

Leu Pro Ser Asn Val Arg Ala Ile His Lys Ser Leu Phe Asp Gly Thr
                325                 330                 335

Leu Gln Gly Ile Glu Leu Thr Asp Lys Ser Ala Phe Ser Phe Gln Gly
            340                 345                 350

His Pro Glu Ala Ser Pro Gly Pro Asn Asp Val Ala Pro Leu Phe Asp
            355                 360                 365

Arg Phe Ile Glu Ala Met Ala Lys Arg Arg
        370                 375

<210> SEQ ID NO 6
<211> LENGTH: 1073
<212> TYPE: PRT
<213> ORGANISM: Pseudomonas syringae

<400> SEQUENCE: 6

Met Pro Lys Arg Thr Asp Ile Lys Ser Ile Leu Ile Leu Gly Ala Gly
  1               5                  10                  15

-continued

```
Pro Ile Val Ile Gly Gln Ala Cys Glu Phe Asp Tyr Ser Gly Ala Gln
            20                  25                  30

Ala Cys Lys Ala Leu Arg Glu Gly Tyr Arg Val Ile Leu Val Asn
        35                  40                  45

Ser Asn Pro Ala Thr Ile Met Thr Asp Pro Ala Met Ala Asp Ala Thr
 50                  55                  60

Tyr Ile Glu Pro Ile Lys Trp Gln Thr Val Ala Lys Ile Ile Glu Lys
 65                  70                  75                  80

Glu Arg Pro Asp Ala Leu Leu Pro Thr Met Gly Gln Thr Ala Leu
                85                  90                  95

Asn Cys Ala Leu Asp Leu Glu Arg Glu Gly Val Leu Glu Lys Phe Gly
            100                 105                 110

Val Glu Met Ile Gly Ala Asn Ala Asp Thr Ile Asp Lys Ala Glu Asp
        115                 120                 125

Arg Ser Arg Phe Asp Lys Ala Met Lys Ser Ile Gly Leu Ala Cys Pro
    130                 135                 140

Arg Ser Gly Ile Ala His Ser Met Glu Glu Ala Asn Ala Val Leu Glu
145                 150                 155                 160

Lys Leu Gly Phe Pro Cys Ile Ile Arg Pro Ser Phe Thr Met Gly Gly
            165                 170                 175

Thr Gly Gly Gly Ile Ala Tyr Asn Arg Glu Glu Phe Glu Glu Ile Cys
        180                 185                 190

Ala Arg Gly Leu Asp Leu Ser Pro Thr Lys Glu Leu Leu Ile Asp Glu
    195                 200                 205

Ser Leu Ile Gly Trp Lys Glu Tyr Glu Met Glu Val Val Arg Asp Lys
210                 215                 220

Lys Asp Asn Cys Ile Ile Val Cys Ser Ile Glu Asn Phe Asp Pro Met
225                 230                 235                 240

Gly Val His Thr Gly Asp Ser Ile Thr Val Ala Pro Ala Gln Thr Leu
            245                 250                 255

Thr Asp Lys Glu Tyr Gln Ile Leu Arg Asn Ala Ser Leu Ala Val Leu
        260                 265                 270

Arg Glu Ile Gly Val Glu Thr Gly Gly Ser Asn Val Gln Phe Gly Ile
    275                 280                 285

Cys Pro Asn Thr Gly Arg Met Val Val Ile Glu Met Asn Pro Arg Val
290                 295                 300

Ser Arg Ser Ser Ala Leu Ala Ser Lys Ala Thr Gly Phe Pro Ile Ala
305                 310                 315                 320

Arg Val Ala Ala Lys Leu Ala Val Gly Tyr Thr Leu Asp Glu Leu Ser
            325                 330                 335

Asn Glu Ile Thr Gly Gly Lys Thr Pro Ala Ser Phe Glu Pro Ser Ile
        340                 345                 350

Asp Tyr Val Val Thr Lys Leu Pro Arg Phe Ala Phe Glu Lys Phe Ala
    355                 360                 365

Lys Ala Asp Ala Arg Leu Thr Thr Gln Met Lys Ser Val Gly Glu Val
370                 375                 380

Met Ala Ile Gly Arg Thr Phe Gln Glu Ser Leu Gln Lys Ala Leu Arg
385                 390                 395                 400

Gly Leu Glu Val Gly Val Cys Gly Leu Asp Pro Lys Leu Asp Leu Ser
            405                 410                 415

His Pro Glu Ser Met Ser Thr Leu Lys Arg Glu Leu Thr Val Pro Gly
        420                 425                 430

Ala Glu Arg Ile Trp Tyr Val Ala Asp Ala Phe Arg Ala Gly Met Thr
    435                 440                 445
```

```
Val Glu Glu Ile Phe Ala Met Asn Met Ile Asp Pro Trp Phe Leu Val
450                 455                 460

Gln Ile Glu Asp Leu Ile Lys Asp Glu Glu Lys Ile Lys Thr Leu Gly
465                 470                 475                 480

Leu Ser Ala Ile Asp Arg Asp Val Met Phe Arg Leu Lys Arg Lys Gly
                485                 490                 495

Phe Ser Asp Ala Arg Leu Ala Lys Leu Leu Gly Val Thr Glu Lys Asn
                500                 505                 510

Leu Arg Thr His Arg His Lys Leu Glu Val Phe Pro Val Tyr Lys Arg
                515                 520                 525

Val Asp Thr Cys Ala Ala Glu Phe Ala Thr Asp Thr Ala Tyr Leu Tyr
                530                 535                 540

Ser Thr Tyr Glu Glu Cys Glu Ala Asn Pro Ser Thr Arg Asp Lys
545                 550                 555                 560

Ile Met Ile Leu Gly Gly Gly Pro Asn Arg Ile Gly Gln Gly Ile Glu
                565                 570                 575

Phe Asp Tyr Cys Cys Val His Ala Ala Leu Ala Leu Arg Glu Asp Gly
                580                 585                 590

Tyr Glu Thr Ile Met Val Asn Cys Asn Pro Glu Thr Val Ser Thr Asp
                595                 600                 605

Tyr Asp Thr Ser Asp Arg Leu Tyr Phe Glu Pro Val Thr Leu Glu Asp
                610                 615                 620

Val Leu Glu Ile Val Arg Val Glu Lys Pro Lys Gly Val Ile Val Gln
625                 630                 635                 640

Tyr Gly Gly Gln Thr Pro Leu Lys Leu Ala Arg Ala Leu Glu Ala Ala
                645                 650                 655

Gly Val Pro Ile Ile Gly Thr Ser Pro Asp Ala Ile Asp Arg Ala Glu
                660                 665                 670

Asp Arg Glu Arg Phe Gln His Met Val Glu Arg Leu Asn Leu Arg Gln
                675                 680                 685

Pro Pro Asn Ala Thr Val Arg Ser Glu Asp Glu Ala Ile Arg Ala Ala
                690                 695                 700

Ala Lys Ile Gly Tyr Pro Leu Val Val Arg Pro Ser Tyr Val Leu Gly
705                 710                 715                 720

Gly Arg Ala Met Glu Ile Val Tyr Gln Glu Asp Glu Leu Lys Arg Tyr
                725                 730                 735

Leu Arg Glu Ala Val Gln Val Ser Asn Asp Ser Pro Val Leu Leu Asp
                740                 745                 750

His Phe Leu Asn Cys Ala Ile Glu Met Asp Val Asp Ala Val Cys Asp
                755                 760                 765

Gly Thr Asp Val Val Ile Gly Ala Ile Met Gln His Ile Glu Gln Ala
                770                 775                 780

Gly Val His Ser Gly Asp Ser Ala Cys Ser Leu Pro Pro Tyr Ser Leu
785                 790                 795                 800

Pro Ala His Ile Gln Asp Glu Met Arg Glu Gln Val Lys Lys Met Ala
                805                 810                 815

Leu Glu Leu Gly Val Val Gly Leu Met Asn Val Gln Leu Ala Leu Gln
                820                 825                 830

Gly Glu Asp Ile Tyr Val Ile Glu Val Asn Pro Arg Ala Ser Arg Thr
                835                 840                 845

Val Pro Phe Val Ser Lys Cys Ile Gly Val Ser Leu Ala Met Ile Ala
850                 855                 860

Ala Arg Val Met Ala Gly Lys Thr Leu Lys Glu Leu Asn Phe Thr Lys
```

-continued

```
865                 870                 875                 880

Glu Ile Ile Pro Asn Phe Tyr Ser Val Lys Glu Ala Val Phe Pro Phe
                885                 890                 895

Ala Lys Phe Pro Gly Val Asp Pro Ile Leu Gly Pro Glu Met Lys Ser
            900                 905                 910

Thr Gly Glu Val Met Gly Val Gly Asp Thr Phe Gly Glu Ala Phe Ala
        915                 920                 925

Lys Ala Gln Met Gly Ala Ser Glu Val Leu Pro Thr Gly Gly Thr Ala
    930                 935                 940

Phe Ile Ser Val Arg Asp Asp Asp Lys Pro Leu Val Glu Ala Val Ala
945                 950                 955                 960

Arg Asp Leu Ile Asn Leu Gly Phe Glu Ile Val Ala Thr Ala Gly Thr
                965                 970                 975

Ala Lys Leu Ile Glu Ala Ala Gly Leu Lys Val Arg Arg Val Asn Lys
            980                 985                 990

Val Thr Glu Gly Arg Pro His Val Val Asp Met Ile Lys Asn Asp Glu
        995                 1000                1005

Val Thr Leu Ile Ile Asn Thr Thr Glu Gly Arg Gln Ser Ile Ala Asp
    1010                1015                1020

Ser Tyr Ser Ile Arg Arg Asn Ala Leu Gln His Lys Ile Tyr Cys Thr
1025                1030                1035                1040

Thr Thr Ile Ala Ala Gly Glu Ala Ile Cys Glu Ala Leu Lys Phe Gly
                1045                1050                1055

Pro Glu Lys Thr Val Arg Arg Leu Gln Asp Leu His Ala Gly Leu Lys
            1060                1065                1070

Ala
```